United States Patent
Badylak et al.

(10) Patent No.: US 11,213,545 B2
(45) Date of Patent: Jan. 4, 2022

(54) ECM HYDROGEL FOR TREATING ESOPHAGEAL INFLAMMATION

(71) Applicant: University of Pittsburgh—Of the Commonwealth System of Higher Education, Pittsburgh, PA (US)

(72) Inventors: Stephen Francis Badylak, West Lafayette, IN (US); Juan Diego Naranjo Gutierrez, Manizales (CO); Lindsey Tamiko Saldin, El Segundo, CA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 16/490,054

(22) PCT Filed: Mar. 2, 2018

(86) PCT No.: PCT/US2018/020758
§ 371 (c)(1),
(2) Date: Aug. 29, 2019

(87) PCT Pub. No.: WO2018/161028
PCT Pub. Date: Sep. 7, 2018

(65) Prior Publication Data
US 2020/0009187 A1 Jan. 9, 2020

Related U.S. Application Data

(60) Provisional application No. 62/465,985, filed on Mar. 2, 2017.

(51) Int. Cl.
*A61K 35/12* (2015.01)
*A61P 1/04* (2006.01)
*A61K 9/06* (2006.01)

(52) U.S. Cl.
CPC .............. *A61K 35/12* (2013.01); *A61K 9/06* (2013.01); *A61P 1/04* (2018.01)

(58) Field of Classification Search
None
See application file for complete search history.

(56) References Cited

U.S. PATENT DOCUMENTS

| | | |
|---|---|---|
| 3,155,095 A | 11/1964 | Brown |
| 4,294,241 A | 10/1981 | Miyata |
| 4,563,350 A | 1/1986 | Nathan et al. |
| 4,582,640 A | 4/1986 | Smestad et al. |
| 4,902,508 A | 2/1990 | Badylak et al. |
| 4,956,178 A | 9/1990 | Badylak et al. |
| 4,978,668 A | 12/1990 | Babbs et al. |
| 5,007,927 A | 4/1991 | Badylak et al. |
| 5,275,826 A | 1/1994 | Badylak et al. |
| 5,281,422 A | 1/1994 | Badylak et al. |
| 5,352,463 A | 10/1994 | Badylak et al. |
| 5,354,274 A | 10/1994 | Demeter et al. |
| 5,372,821 A | 12/1994 | Badylak et al. |
| 5,445,833 A | 8/1995 | Badylak et al. |
| 5,516,533 A | 5/1996 | Badylak et al. |
| 5,554,389 A | 9/1996 | Badylak et al. |
| 5,573,784 A | 11/1996 | Badylak et al. |
| 5,641,518 A | 6/1997 | Badylak et al. |
| 5,645,860 A | 7/1997 | Knapp, Jr. et al. |
| 5,695,998 A | 12/1997 | Badylak et al. |
| 5,711,969 A | 1/1998 | Patel et al. |
| 5,753,267 A | 5/1998 | Badylak et al. |
| 5,755,791 A | 5/1998 | Whitson et al. |
| 5,762,966 A | 6/1998 | Knapp, Jr. et al. |
| 5,866,414 A | 2/1999 | Badylak et al. |
| 5,885,619 A | 3/1999 | Patel et al. |
| 5,955,110 A | 9/1999 | Patel et al. |
| 5,968,096 A | 10/1999 | Whitson et al. |
| 5,997,575 A | 12/1999 | Whitson et al. |
| 6,087,157 A | 7/2000 | Badylak et al. |
| 6,096,347 A | 8/2000 | Geddes et al. |
| 6,099,567 A | 8/2000 | Badylak et al. |
| 6,126,686 A | 10/2000 | Badylak et al. |
| 6,187,039 B1 | 2/2001 | Hiles et al. |
| 6,241,774 B1 | 6/2001 | Shimizu |
| 6,241,981 B1 | 6/2001 | Cobb et al. |

(Continued)

FOREIGN PATENT DOCUMENTS

| | | |
|---|---|---|
| WO | WO 2000/032209 A2 | 6/2000 |
| WO | WO 2003/059284 | 7/2003 |

(Continued)

OTHER PUBLICATIONS

Badylak, "Esophageal tissue engineering," McGowan Institute for Regenerative Medicine, hhtp://www.mirm.pitt.edu/Badylak/projects/Esophageal_Tissue_Engineering.asp, 3 pages (printed to PDF on Dec. 21, 2016).

International Search Report and Written Opinion from parent PCT Application No. PCT/US2018/020758, 8 pages (dated May 8, 2018).

Keane et al., "Restoring mucosal barrier function and modifying macrophage phenotype with an extracellular matrix hydrogel: Potential therapy for ulcerative colitis," *Journal of Crohn's and Colitis* 11(3): 360-368 (Epub Sep. 10, 2016).

(Continued)

*Primary Examiner* — Qiuwen Mi

(74) *Attorney, Agent, or Firm* — Klarquist Sparkman, LLP

(57) ABSTRACT

Methods are disclosed for inhibiting esophageal inflammation in a subject, that include administering to the esophagus of the subject with esophageal inflammation a therapeutically effective amount of an extracellular matrix (ECM) hydrogel. Methods are also disclosed for reducing esophageal stricture. Compositions are disclosed that include an esophageal extracellular matrix (ECM) hydrogel.

18 Claims, 18 Drawing Sheets

(56) References Cited

U.S. PATENT DOCUMENTS

| | | | |
|---|---|---|---|
| 6,264,992 B1 | 7/2001 | Voytik-Harbin et al. |
| 6,331,319 B1 | 12/2001 | Badylak et al. |
| 6,444,229 B2 | 1/2002 | Voytik-Harbin et al. |
| 6,375,989 B1 | 4/2002 | Badylak et al. |
| 6,379,710 B1 | 4/2002 | Badylak |
| 6,448,076 B2 | 9/2002 | Dennis et al. |
| 6,475,232 B1 | 11/2002 | Babbs et al. |
| 6,485,723 B1 | 11/2002 | Badylak et al. |
| 6,576,265 B1 | 6/2003 | Spievack |
| 6,579,538 B1 | 6/2003 | Spievack |
| 6,653,291 B1 | 11/2003 | Badylak et al. |
| 6,696,270 B2 | 2/2004 | Badylak et al. |
| 6,783,776 B2 | 8/2004 | Spievack |
| 6,793,939 B2 | 9/2004 | Badylak |
| 6,849,273 B2 | 2/2005 | Spievack |
| 6,852,339 B2 | 2/2005 | Spievack |
| 6,861,074 B2 | 3/2005 | Spievack |
| 6,887,495 B2 | 5/2005 | Spievack |
| 6,890,562 B2 | 5/2005 | Spievack |
| 6,890,563 B2 | 5/2005 | Spievack |
| 6,890,564 B2 | 5/2005 | Spievack |
| 6,893,666 B2 | 5/2005 | Spievack |
| 6,918,396 B1 | 7/2005 | Badylak et al. |
| 6,962,814 B2 | 11/2005 | Mitchell et al. |
| 7,175,841 B2 | 2/2007 | Badylak et al. |
| 7,326,571 B2 | 2/2008 | Freyman |
| 7,402,319 B2 | 7/2008 | Schmidt et al. |
| 7,482,025 B2 | 1/2009 | Badylak |
| 7,771,717 B2 | 8/2010 | Badylak et al. |
| 7,776,596 B2 | 8/2010 | Badylak |
| 7,795,022 B2 | 9/2010 | Badylak |
| 7,815,686 B2 | 10/2010 | Badylak |
| 7,820,634 B2 | 10/2010 | Badylak et al. |
| 7,919,121 B2 | 4/2011 | Badylak et al. |
| 8,003,131 B2 | 8/2011 | Badylak |
| 8,021,692 B2 | 9/2011 | Hiles et al. |
| 8,029,774 B2 | 10/2011 | Beckman et al. |
| 8,084,048 B2 | 12/2011 | Badylak |
| 8,192,763 B2 | 6/2012 | Johnson |
| 8,241,908 B2 | 8/2012 | Qian et al. |
| 8,361,503 B2 | 1/2013 | Badylak et al. |
| 8,409,625 B2 | 4/2013 | Badylak |
| 8,535,719 B2 | 9/2013 | Badylak et al. |
| 8,647,677 B2 | 2/2014 | Badylak et al. |
| 8,691,276 B2 | 4/2014 | Badylak et al. |
| 8,716,438 B2 | 5/2014 | Agrawal et al. |
| 8,741,352 B2 | 6/2014 | Hodde et al. |
| 8,802,436 B1 | 8/2014 | Kentner et al. |
| 8,927,003 B2 | 1/2015 | Badylak et al. |
| 9,119,831 B2 | 9/2015 | Kentner et al. |
| 9,226,996 B2 | 1/2016 | Moro et al. |
| 9,277,999 B2 | 3/2016 | Badylak et al. |
| 9,314,340 B2 | 4/2016 | Badylak et al. |
| 9,340,602 B2 | 5/2016 | Agrawal et al. |
| 9,364,580 B2 | 6/2016 | Moro et al. |
| 9,421,307 B2 | 8/2016 | Amoroso et al. |
| 9,474,829 B2 | 10/2016 | Kentner et al. |
| 9,480,776 B2 | 11/2016 | Badylak et al. |
| 9,522,216 B2 | 12/2016 | Moro et al. |
| 9,795,713 B2 | 10/2017 | Kentner et al. |
| 9,814,744 B2 | 11/2017 | Badylak et al. |
| 9,848,987 B2 | 12/2017 | Badylak et al. |
| 9,861,662 B2 | 1/2018 | Badylak et al. |
| 10,004,827 B2 | 6/2018 | Badylak et al. |
| 10,005,827 B2 | 6/2018 | Badylak et al. |
| 10,092,676 B2 | 10/2018 | Amoroso et al. |
| 10,213,526 B2 | 2/2019 | Badylak et al. |
| 10,286,119 B2 | 5/2019 | Badylak et al. |
| 10,729,813 B2 | 8/2020 | Badylak et al. |
| 10,736,991 B2 | 8/2020 | Badylak et al. |
| 2002/0115208 A1 | 8/2002 | Mitchell et al. |
| 2003/0012822 A1 | 1/2003 | Voytik-Harbin et al. |
| 2004/0078076 A1 | 4/2004 | Badylak et al. |
| 2004/0175366 A1 | 9/2004 | Badylak |
| 2004/0176855 A1 | 9/2004 | Badylak |
| 2004/0187877 A1 | 9/2004 | Badylak et al. |
| 2004/0191226 A1 | 9/2004 | Badylak |
| 2006/0134079 A1 | 6/2006 | Sih et al. |
| 2006/0201996 A1 | 9/2006 | Hodde |
| 2007/0014860 A1* | 1/2007 | Rosenthal ............ A61K 47/10 424/486 |
| 2007/0135906 A1 | 6/2007 | Badylak et al. |
| 2008/0107750 A1 | 5/2008 | Hodde et al. |
| 2010/0196480 A1 | 8/2010 | Hiles et al. |
| 2011/0184439 A1 | 7/2011 | Anderson et al. |
| 2011/0224484 A1 | 9/2011 | Case et al. |
| 2013/0202563 A1 | 8/2013 | Badylak et al. |
| 2014/0356331 A1 | 12/2014 | Badylak et al. |
| 2016/0045552 A1 | 2/2016 | Ramer et al. |
| 2017/0049932 A1 | 2/2017 | Badylak et al. |
| 2018/0043057 A1 | 2/2018 | Kentner et al. |
| 2018/0200405 A1 | 7/2018 | Badylak et al. |
| 2018/0243473 A1 | 8/2018 | Badylak et al. |
| 2019/0015552 A1 | 1/2019 | Badylak et al. |
| 2019/0076574 A1 | 3/2019 | Ramer et al. |
| 2019/0117837 A1 | 4/2019 | Badylak et al. |
| 2020/0009187 A1 | 1/2020 | Badylak et al. |
| 2020/0030495 A1 | 1/2020 | Badylak et al. |
| 2020/0069738 A1 | 3/2020 | Badylak et al. |
| 2020/0261624 A1 | 8/2020 | Crapo et al. |
| 2021/0106526 A1 | 4/2021 | Badylak et al. |

FOREIGN PATENT DOCUMENTS

| | | |
|---|---|---|
| WO | WO 2003/059284 A2 | 7/2003 |
| WO | WO 2005/020847 | 3/2005 |
| WO | WO 2008/109407 A2 | 8/2008 |
| WO | WO 2018/161034 A1 | 9/2018 |
| WO | WO 2018/204848 A1 | 11/2018 |

OTHER PUBLICATIONS

Keane et al., "Tissue-specific effects of esophageal extracellular matrix," *Tissue Engineering: Part A* 21(17 and 18): 2293-2299 (2015).

Londono et al., "Esophagus and regenerative medicine," *World Journal of Gastroenterol* 18(47): 6894-6899 (Dec. 21, 2012).

Saldin et al., "Extracellular matrix hydrogels from decellularized tissues: Structure and function," *Acta Biomaterialia* 49:1-15 (Epub Dec. 1, 2016).

Badylak et al., "Esophageal reconstruction with ECM and muscle tissue in a dog model," *J Surg Res.* 128(1):87-97 (Sep. 1, 2005).

Badylak et al., "Resorbable bioscaffold for esophageal repair in a dog model," *J Pediatr Surg.* 35(7): 1097-1103 (Jul. 1, 2000).

Freytes et al., "Preparation and rheological characterization of a gel form of the porcine urinary bladder matrix," *Biomaterials* 29(11): 1630-1637 (available on-line Jan. 16, 2008).

Keane et al., "Tissue-specific effects of esophageal extracellular matrix," *Tissue Eng. Part A* 21(17-18): 2293-2300 (published on-line Aug. 12, 2015).

Wolf et al., "A hydrogel derived from decellularized dermal extracellular matrix," *Biomaterials* 33(29): 7028-7038 (Oct. 2012).

Abed et al. "A biocompatible polysaccharide hydrogel-embedded polypropylene mesh for enhanced tissue integration in rats." *Tissue Engineering*, 2008, 14(4):519-527.

Badylak et al., "ESOPHAGEL ™: Revolutionizing the way we treat esophageal disease," University of Pittsburgh Innovation Institute, Pamphlet, ID: 3936 (2 pages), downloaded on Oct. 19, 2017.

Badylak SF, Arnoczky S, Plouhar P, Haut R, Mendenhall V, Clarke R, Horvath C. Naturally occurring extracellular matrix as a scaffold for musculoskeletal repair.*Clin Orthop*, 1999. (367 Suppl): S333-343. Pmid: 10546657.

Badylak SF, Freytes DO, Gilbert TW. Extracellular matrix as a biological scaffold material: Structure and function. *Acta Biomater*, 2009. 5 (1): 1-13. PMID: 18938117. (Reprint, 2015. PMID: 26235342.).

Badylak SF, Hoppo T, Nieponice A, Gilbert TW, Davison JM, Jobe BA. Esophageal preservation in five male patients after endoscopic inner-layer circumferential resection in the setting of superficial

(56) References Cited

OTHER PUBLICATIONS cancer: a regenerative medicine approach with a biologic scaffold. *Tissue Eng Part A*, 2011. 17 (11-12): 1643-1650. PMID: 21306292. PMCID: PMC3098955.
Badylak SF. The extracellular matrix as a biologic scaffold material. *Biomaterials*, 2007. 28 (25): 3587-3593. PMID: 17524477.
Badylak SF. Xenogeneic extracellular matrix as a scaffold for tissue reconstruction. *Transpl Immunol.*, 2004. 12 (3-4): 367-377. PMID: 15157928.
Boccafoshi et al., "Decellularized biological matrices: an interesting approach for cardiovascular tissue repair and regeneration", *J Tissue Eng Regen Med*, 2015, pp. 1648-1657.
Chan et al.; "Viscosities of Injectable Biomaterials in Vocal Fold Augmentation Surgery"; *NCVS Status and Progress Report*; 1997; pp. 119-126; vol. 11.
Crapo et al., "An Overview of Tissue and Whole Organ Decellularization Processes", *Biomaterials*, Apr. 2011, 32(12), pp. 3233-3243, pp. 1-23. (Year: 2011).
Crapo et al., Small Intestinal Submucosa Gel as a Potential Scaffolding Material for Cardiac Tissue Engineering, Acta Biomater, 2010, vol. 6, No. 6, pp. 2091-2096.
Dearth CL, Keane TJ, Carruthers CA, Reing JE, Huleihel L, Ranallo CA, Kollar EW, Badylak SF. The effect of terminal sterilization on the material properties and in-vivo remodeling of a porcine dermal biologic scaffold. Acta Bio, 2016. 33:78-87. PMID: 26826528.
DeMeester SR, DeMeester TR. The diagnosis and management of Barrett's esophagus. *Adv Surg*. 1999;33:29-68.
Dequach et al., Injectable skeletal muscle matrix hydrogel promotes neovascularization and muscle cell infiltration in a hindlimb ischemia model, *Eur Cell Mater*, 2012, vol. 23, pp. 400-412.
Doede et al., Unsuccessful alloplastic esophageal replacement with porcine small intestinal submucosa, *Artificial Organs*, 2009, pp. 328-333, vol. 33, No. 4.
Faulk et al., "ECM hydrogel coating mitigates the chronic inflammatory response to polypropylene mesh", *Biomaterials*, (2014), p. 8585-8595, 35.
Faust A, Kandakatla, van der Merwe Y, Huleihel L, Hussey GS, Ren T, Johnson S, Badylak SF, Steketee MB. Urinary bladder extracellular matrix hydrogels and matrix-bound vesicles differentially regulate central nervous system neuron viability and axon growth and branching. *Journal of Biomaterials Applications*, 2017. 31 (9): 1277-1295. PMID: 28447547.
Faust et al., "Urinary bladder extracellular matrix hydrogels and matrix-bound vesicles differentially regulate central nervous system neuron viability and axon growth and branching," *Journal of Biomaterials Applications* 31(9): 1277-1295 (E-pub Mar. 9, 2017) (Abstract only).
Fercana GR, Yemeni S, Billaud M, Hill JC, VanRyzin P, Richards TD, Sicari B, Badylak SF, Johnson S, Campbell PG, Gleason TG and Phillippi JA. Perivascular Extracellular Matrix Hydrogels Mimic Native Matrix Microarchitecture and Promote Angiogenesis via Basic Fibroblast Growth Factor. *Biomaterials*, 2017. 123: 142-154. PMID: 28167924. Pmcid: PMC5319845.
Freytes DO, Tullius RS, Valentin JE, Stewart-Akers AM, Badylak SF. Hydrated versus lyophilized forms of porcine extracellular matrix derived from the urinary bladder. *J Biomed Mater Res* A, 2008. 87(4): 862-872. doi:10.1002/jbm.a.31821 PMID: 18228251.
Freytes, DO, Lee AS, Badylak SF. Porcine Urinary Bladder Matrix Derived Gel for Tissue Engineering Applications. *Regenerate World Congress and Society for Biomaterials*: 2006. Pittsburgh, PA. (Poster and Abstract).
Ghuman H, Gerwig M, Nicholls FJ, Liu J; Donnelly J; Badylak SF, Modo M. Long-term retention of ECM hydrogel after implantation into a sub-acute stroke cavity reduces lesion vol. *Acta Biomater* 2017. 63 (2017) 50-63. PMID: 28917705.
Gilbert TW, Sellaro TL, Badylak SF. Decellularization of tissues and organs. *Biomaterials*, 2006. 27 (19): 3675-3683. PMID: 16519932. PMCID: NA.
Gilbert TW, Stolz DB, Biancaniello F, Simmons-Byrd A, Badylak SF. Production and characterization of ECM powder: implications for tissue engineering applications. *Biomaterials*, 2005. 26 (12): 1431-1435. PMID: 15482831.
Heitmiller RF, Fischer A, Liddicoat JR. Cervical esophagogastric anastomosis: results following esophagectomy for carcinoma. *Dis Esophagus*. 1999; 12(4):264-9.
Hinderer et al., "ECM and ECM-like materials—Biomaterials for applications in regenerative medicine and cancer therapy," *Advanced Drug Delivery Reviews* 97: 260-269 (Epub Dec. 3, 2015).
Hong Y, Huber A, Takanari K, Amoroso NJ, Hashizume R, Badylak SF, Wagner WR. Mechanical properties and in vivo behavior of a biodegradable synthetic polymer microfiber-extracellular matrix hydrogel biohybrid scaffold. *Biomaterials*, 2011. 32 (13): 3387-3394. PMID: 21303718. PMCID: PMC3184831.
Huber JE, Spievack A, Simmons-Byrd A, Ringel RL, Badylak SF. Extracellular matrix as a scaffold for laryngeal reconstruction. *Ann Otol Rhinol Laryngol*, 2003. 112 (5): 428-433. PMID: 12784982. PMCID: NA.
Lannettoni MD, Whyte RI, Orringer MB. Catastrophic complications of the cervical esophagogastric anastomosis. *J Thorac Cardiovasc Surg*. Nov. 1995;110(5):1493-500; discussion 1500-1.
Ishihara et al., "Application of hydrogels as submucosal fluid cushions for endoscopic mucosal resection and submucosal dissection," *J Artif Organs*. 18(3): 191-198 (ePub May 23, 2015) (Abstract only).
Jin T, Nicholls F, Crum W, Ghuman H, Badylak SF, Modo M. Diamagnetic chemical exchange saturation transfer (diaCEST) affords magnetic resonance imaging of extracellular matrix hydrogel implantation in a rat model of stroke. *Biomaterials*, 2017. 113:176-190. PMID: 27816001. PMCID: PMC5121043.
Jobe et al., Endoscopic appraisal of the gastroesophageal value after antireflux surgery, *Am J Gastroenterology*, Feb. 2004, pp. 233-243, vol. 99, issue 2.
Jung and Park, "Submucosal injection solutions for endoscopic mucosal Resection and endoscopic submucosal dissection of gastrointestinal neoplasms," *Gastrointestinal Intervention* 2: 73-77 (2013).
Kakushima and Fujishiro, "Endoscopic submucosal dissection for gastrointestinal neoplasms," *World J Gastroenterol*. 14(19): 2962-2967 (May 21, 2008).
Keane TJ, Dziki JL, Castleton A, Faulk DM, Messerschmidt V, Londono R, Reing JE, Velankar SS, Badylak SF. Preparation and Characterization of a Biologic Scaffold and Hydrogel from Colonic Mucosa. *JBMR Part B*. 2017. 105(2):291-306. PMID: 26506408.
Keane TJ, Londono R, Carey RM, Carruthers CA, Reing JE, Dearth CL, D'Amore A, Medberry CJ, Badylak SF. Preparation and characterization of a biologic scaffold from esophageal mucosa. *Biomaterials*. 2013. 34(28):6729-37. PMID: 3777917; PMCID: PMC3727430.
Keane TJ, Swinehart I, Badylak SF. Methods of Tissue Decellularization Used for Preparation of Biologic Scaffolds and In-vivo Relevance. *Methods*. 2015. 84:25-34. PMID: 25791470.
Lehman GA. Injectable and bulk-forming agents for enhancing the lower esophageal sphincter. *Am J Med*. Aug. 1, 20038;115 Suppl 3A:188S-91 S.
Londono R, Jobe BA, Hoppo T, Badylak SF. Esophagus and regenerative medicine. *World J Gastroenterol*. 2012. 18(47):6894-9. 23322986. PMCID: 3531672.
Massensini AR, Ghuman H, Saldin LT, Medberry CJ, Keane TJ, Nicholls FJ, Velankar SS, Badylak SF, Modo M. Concentration-dependent rheological properties of ECM hydrogel for intracerebral delivery to a stroke cavity. *Acta Biomateriala*. 2015. 27: 116-130. PMID: 26318805. PMCID: PMC4609617.
Mazzitelli S, Luca G, Mancuso F, Calvitti M, Calafiore R, Nastruzzi C, Johnson S, Badylak SF. Production and characterization of engineered alginate-based microparticles containing ECM powder for cell/tissue engineering applications. *Acta Biomater*, 2011. 7 (3): 1050-1062. PMID: 20950716.
Medberry CJ, Crapo PM, Siu BF, Carruthers CA, Wolf MT, Nagarkar SP, Agrawal V, Jones KE, Kelly J, Johnson SA, Velankar SS, Watkins SC, Modo M, Badylak SF. Hydrogels derived from central nervous system extracellular matrix. *Biomaterials*. 2013. 34(4): 1033-40. PMID: 23158935. PMCID: 3512573.

(56) References Cited

OTHER PUBLICATIONS

Narita et al., "Immune responses in patients with esophageal cancer treated with SART1 peptide-pulsed dendritic cell vaccine," *International Journal of Oncology* vol. 46(4): 1699-1709, published on-line Jan. 23, 2015.

Nieponice A, Ciotola FF, Nachman F, Jobe BA, Hoppo T, Londono R, Badylak S, Badaloni AE. Patch esophagoplasty: esophageal reconstruction using biologic scaffolds. *Ann Thorac Surg.* 2014. 97(1):283-8. PMID: 24266951.

Nieponice A, Gilbert TW, Badylak SF. Reinforcement of esophageal anastomoses with an extracellular matrix scaffold in a canine model. *Ann Thorac Surg*, 2006. 82 (6): 2050-2058. PMID: 17126109.

Nieponice A, McGrath K, Qureshi I, Beckman EJ, Luketich JD, Gilbert TW, Badylak SF. An extracellular matrix scaffold for esophageal stricture prevention after circumferential EMR. *Gastrointest Endosc*, 2009. 69 (2): 289-296. PMID: 18657808.

Orringer MB, Marshall B, Iannettoni MD. Transhiatal esophagectomy for treatment of benign and malignant esophageal disease. *World J Surg.* Feb. 2001;25(2): 196-203.

Orringer MB, Stirling MC. Cervical esophagogastric anastomosis for benign disease. Functional results. *J Thorac Cardiovasc Surg.* Dec. 1988;96(6):887-93.

Ringel RL, Kahane JC, Hillsamer PJ, Lee AS, Badylak SF. The application of tissue engineering procedures to repair the larynx. *J Speech Lang Hear Res*, 2006. 49 (1): 194-208. PMID: 16533084.

Rizk NP, et al. The impact of complications on outcomes after resection for esophageal and gastroesophageal junction carcinoma. *J Am Coll Surg.* Jan. 2004;198(1):42-50.

Saldin LT, Cramer MC, Velankar SS, White LJ, Badylak SF. Extracellular Matrix Hydrogels from Decellularized Tissues: Structure and Function. *Acta Bio*, 2017. 49: 1-15. PMID: 27915024. PMCID: PMC5253110.

Santucci RA, Barber TD. Resorbable extracellular matrix grafts in urologic reconstruction. *Int Braz J Urol.* May 2005-Jun. 31 (3): 192-203. Review.

Sawkins MJ, Bowen W, Dhadda P, Markides H, Sidney LE, Taylor AJ, Rose FR, Badylak SF, Shakesheff KM, White LJ. Hydrogels derived from demineralized and decellularized bone extracellular matrix. *Acta Biomater.* 2013. 9(8):7865-73. PMID: 23624219; PMCID: PMC3711237.

Schuchert et al., Impact of anastomotic leak on outcomes after transhiatal esophagectomy, *Surgery*, Oct. 2010, pp. 831-838, vol. 148, issue 4.

Seif-Naraghi et al., Design and Characterization of an Injectable Pericardial Matrix Gel: A Potentially Autologous Scaffold for Cardiac Tissue Engineering, *Tissue Eng Part A*, 2010, vol. 16, No. 6, pp. 2017-27.

Stein HJ, Feith M, Mueller J, Werner M, Siewert JR. Limited resection for early adenocarcinoma in Barrett's esophagus. *Ann Surg.* Dec. 2000;232(6):733-42.

Stuart et al. Characterization of Gels Composed of Blends of Collagen I, Collagen III, and Chondroitin Sulfate, *Biomacromolecules*, 2009, vol. 10, No. 1, pp. 25-31.

Stuart et al.; "Influence of chondroitin sulfate on collagen gel structure and mechanical properties at physiologically relevant levels"; *Biopolymers*; 2008; pp. 841-851; vol. 89.

Takanari K, Hong Y, Hashizume R, Huber A, Amoroso NJ, D'Amore A, Badylak SF, Wagner WR. Abdominal wall reconstruction by a regionally distinct biocomposite of extracellular matrix digest and a biodegradable elastomer. *J Tissue Eng Regen Med.* 2016 10(9):748-61. PMID: 24376045.

Tukmachev D, Forostyak S, Zaviskova K, Koci Z, Vackova I, Vyborny K, Sandvig I, Sandvig A, Medberry C, Badylak SF, Sykova E, Kubinova S. Injectable extracellular matrix hydrogels as scaffolds for spinal cord injury repair. *Tissue Engineering Part A* Feb. 2016; 22 (3-4):306-17. PMID: 26729284. Pmcid: PMC4799710.

Uraoka et al., "Submucosal injection solution for gastrointestinal tract endoscopic mucosal resection and endoscopic submucosal dissection," *Drug Design, Development and Theory 2*: . 131-138 (2008).

Wang et al., "Preparation and characterization of pro-angiogenic gel derived from small intestinal submucosa", *Acta Biomaterialia*, 2016, vol. 29, pp. 135-148.

Whyte RI, Orringer MB. Surgery for Carcinoma of the Esophagus: The Case for Transhiatal Esophagectomy. *Semin Radial Oncol.* Jul. 1994;4(3): 146-156.

Witteman BP, Foxwell TJ, Monsheimer S, Gelrud A, Eid GM, Nieponice A, O'Rourke RW, Hoppo T, Bouvy ND, Badylak SF, Jobe BA. Transoral Endoscopic Inner Layer Esophagectomy: Management of High-Grade Dysplasia and Superficial Cancer with Organ Preservation. *J Gastrointest Surg*, 2009. 13 (12): 2104-2112. PMID: 19826883.

Wood JD, Simmons-Byrd A, Spievack AR, Badylak SF. Use of a particulate extracellular matrix bioscaffold for treatment of acquired urinary incontinence in dogs. *J Am Vet Med Assoc.*, 2005. 226 (7): 1095-1097. PMID: 15825734.

Yildirim S, Koksal H, Celayir F, Erdem L, Oner M, Baykan A. Colonic interposition vs. gastric pull-up after total esophagectomy. *J Gastrointest Surg.* Sep. 2004-Oct;8(6):675-8.

Zhang L, Zhang F, Weng Z, Brown BN, Yan H, Ma XM, Vosler PS, Badylak SF, Dixon CE, Cui XT, Chen J. Effect of an inductive hydrogel composed of urinary bladder matrix upon functional recovery following traumatic brain injury. *Tissue Eng Part A*. 2013. 19(17-18): 1909-18. PubMed PMID: 23596981; PMCID: PMC3726021.

* cited by examiner

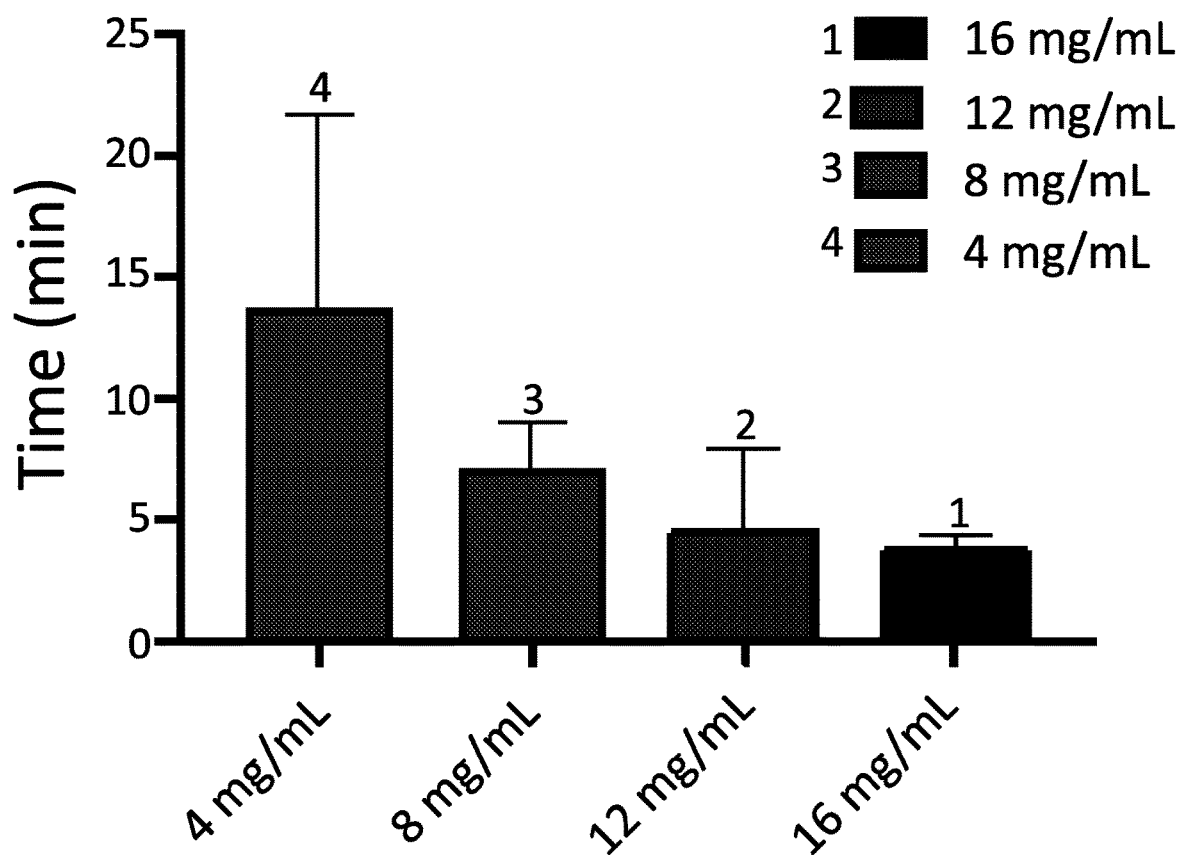

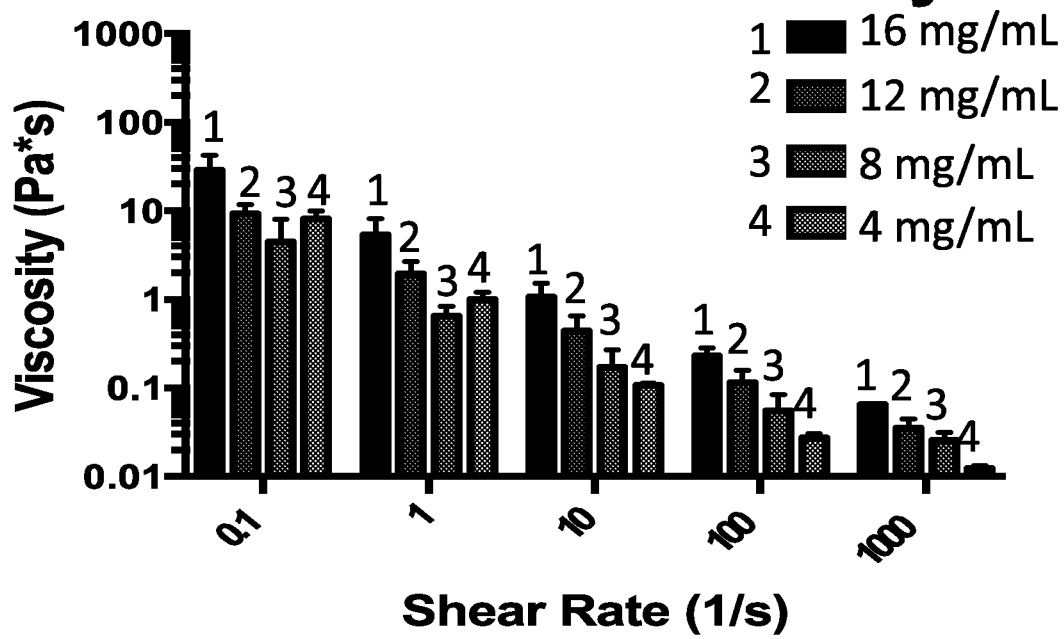
FIG. 4A eECM flow viscosity
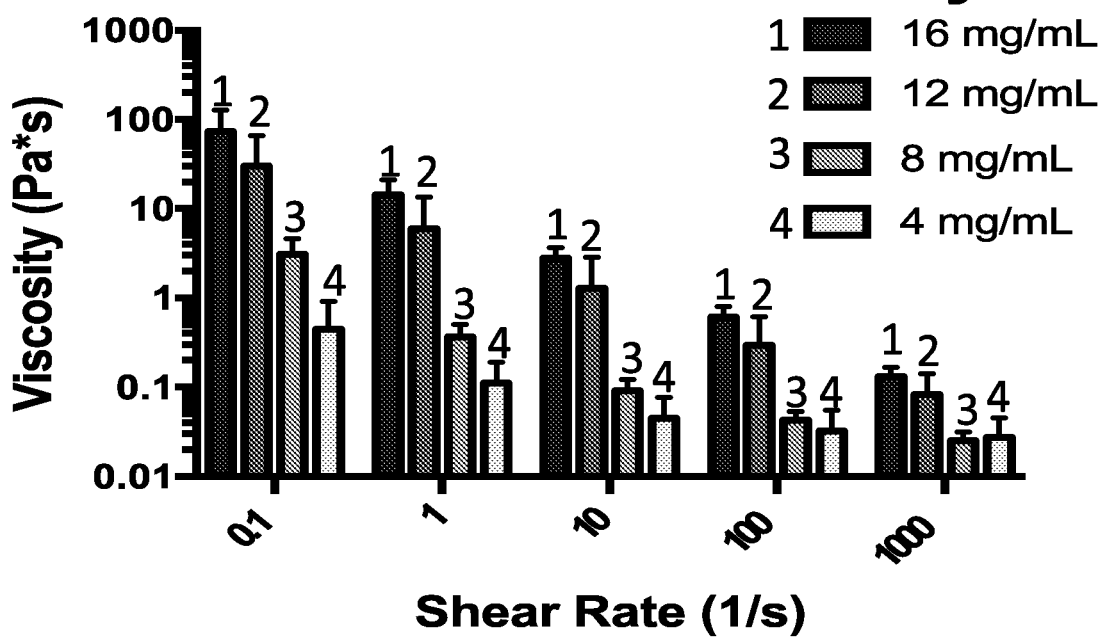
FIG. 4B MIRM5 flow viscosity

FIG. 5B MIRM5 time sweep
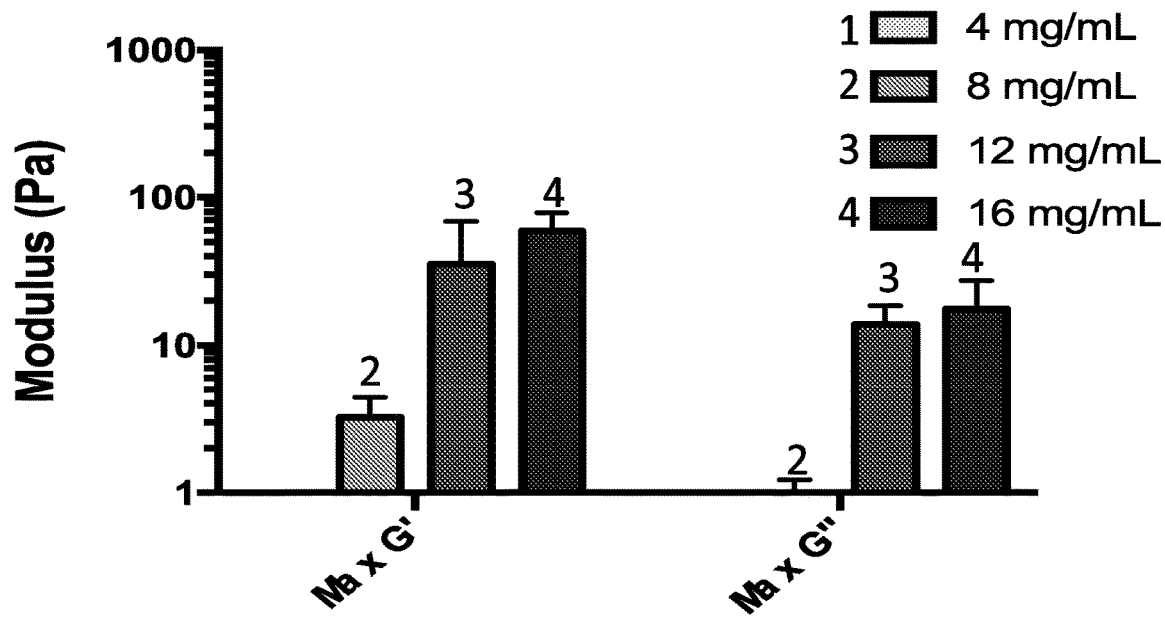
FIG. 5C UBM Time Sweep
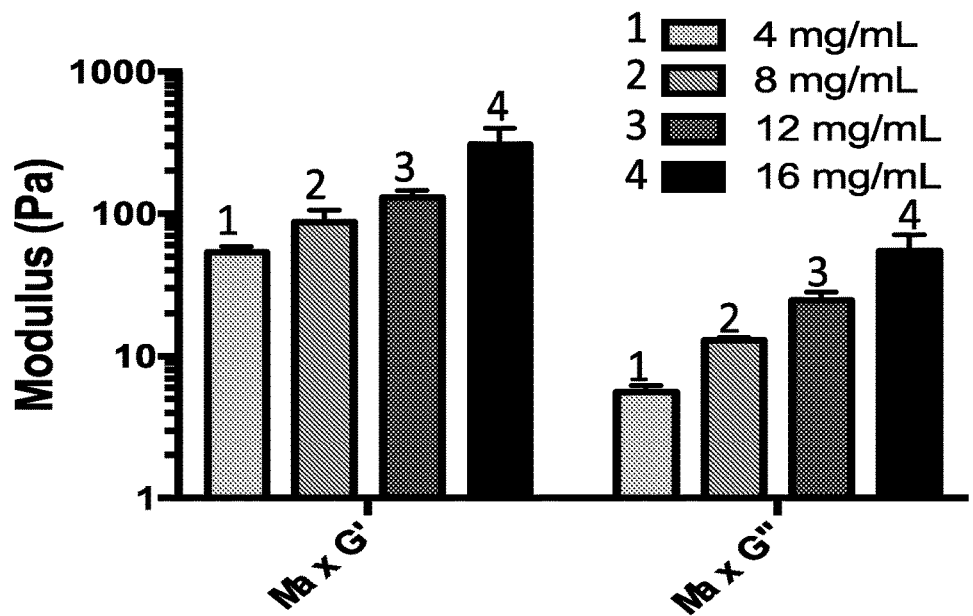

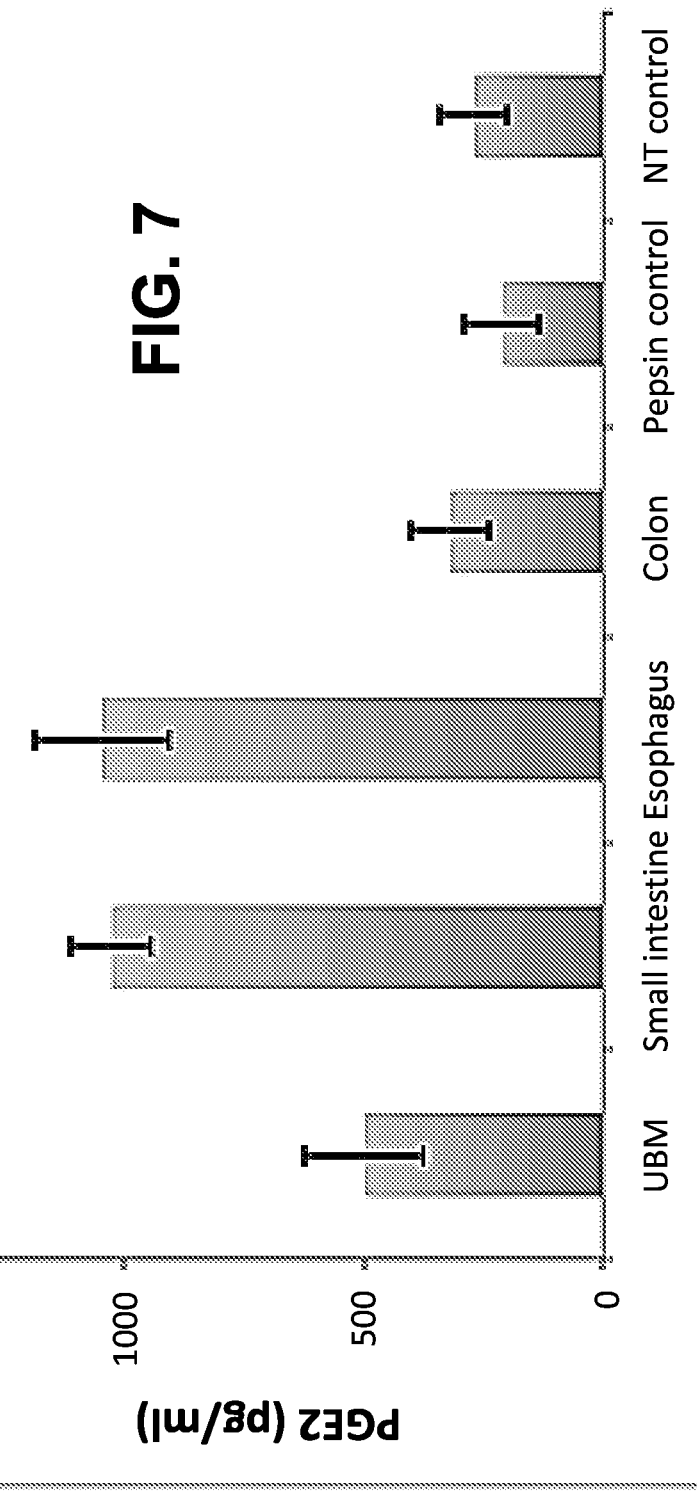

FIG. 8A
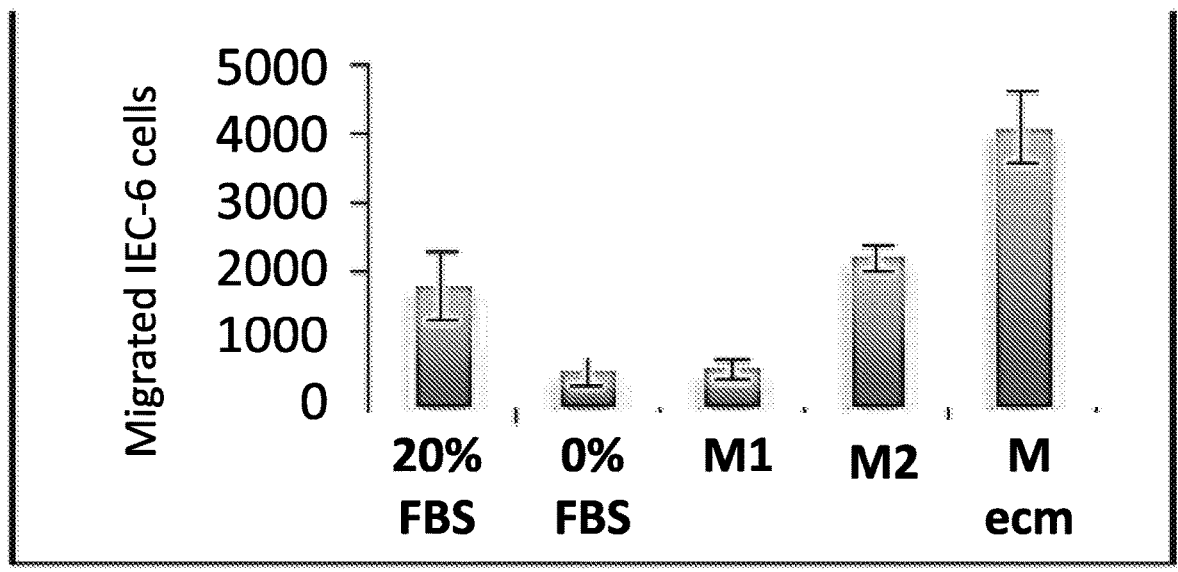
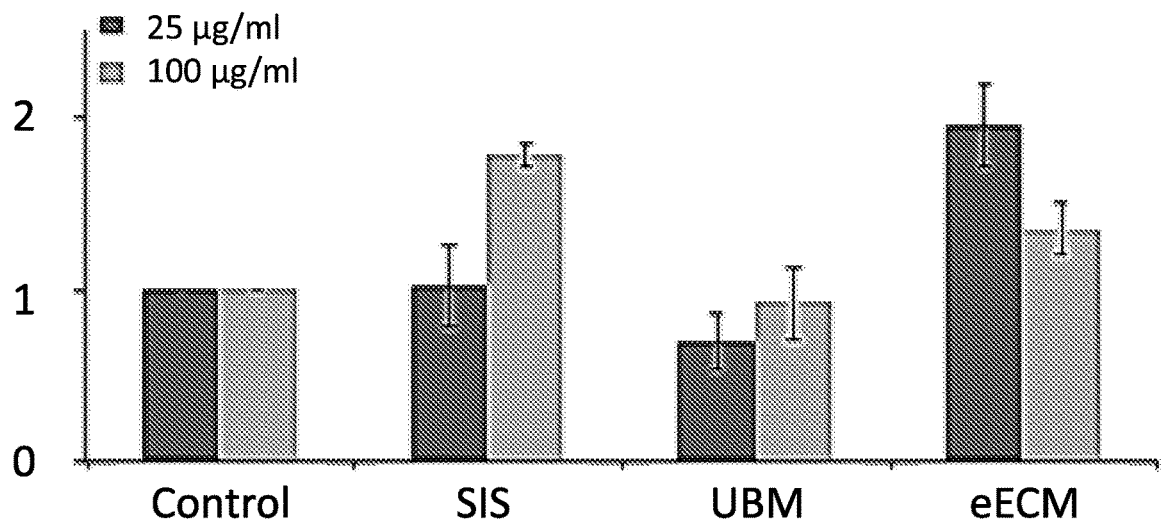
FIG. 8B

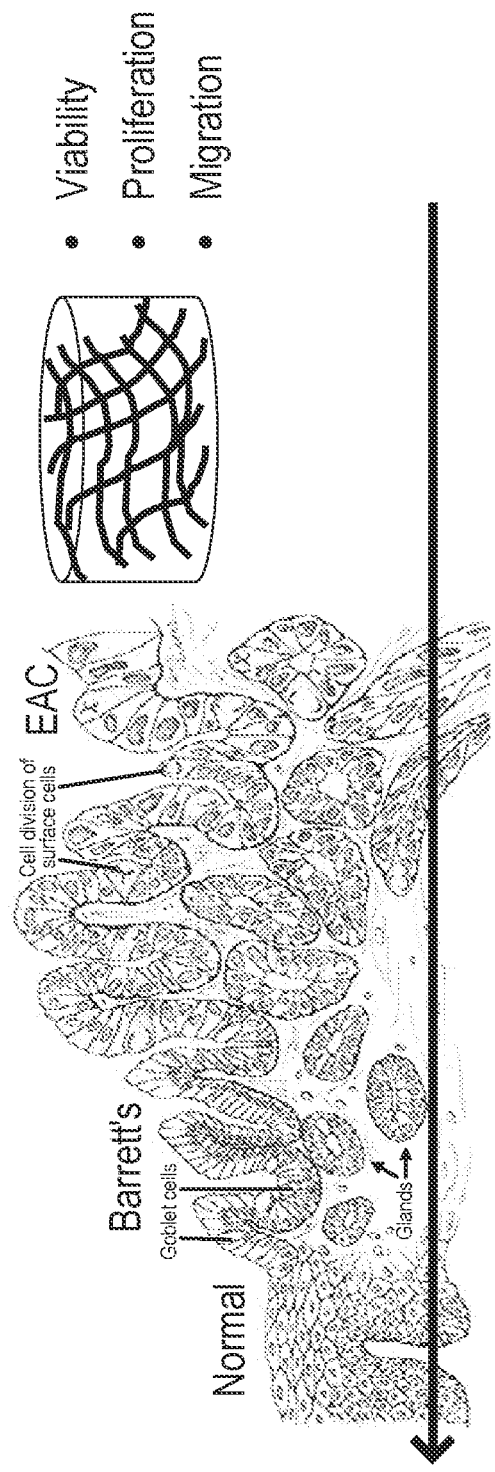
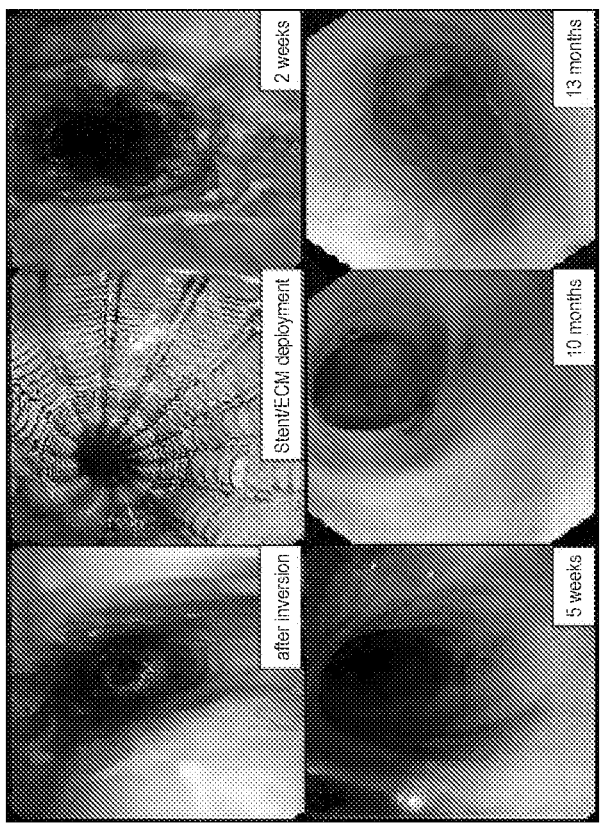
FIG. 9

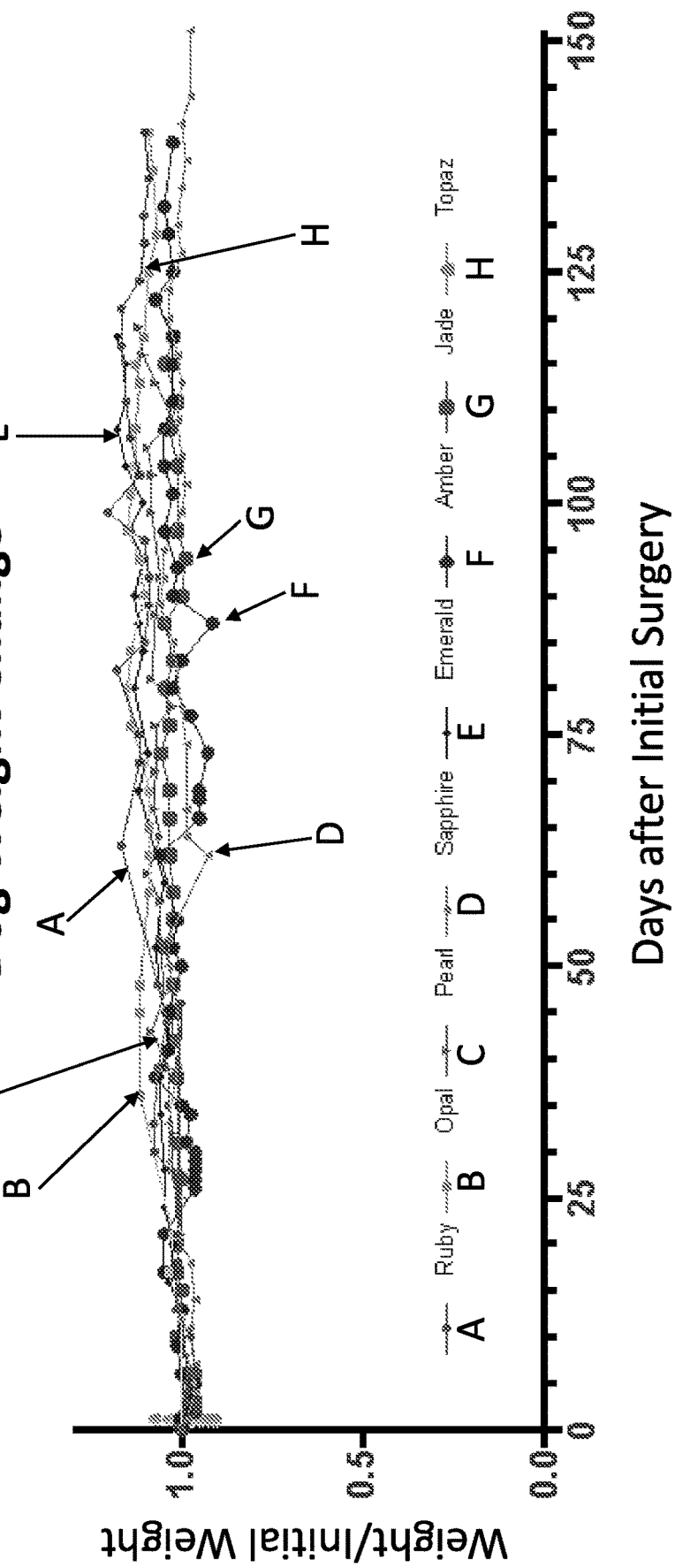

FIG. 12B

| ANALYSIS | Before ECM Treatment (n=3) | After 30 days ECM Treatment (n=3) | Normal Range | Units |
|---|---|---|---|---|
| ALB (Albumin) | 3.325 | 3.4 | 2.5 – 4.4 | G/DL |
| ALP (Alkaline Phosphatase) | 15 | 17.33 | 20 – 150 | U/L |
| ALT (Alanine aminotransferase) | 42.25 | 57.67 | 10 – 118 | U/L |
| AMY (Amylase) | 339 | 427 | 200 – 1200 | U/L |
| TBIL (Total Bilirubin) | 0.275 | 0.2 | 0.1 – 0.6 | MG/DL |
| BUN (Blood urea nitrogen) | 12.75 | 11.67 | 7 – 25 | MG/DL |
| CA (Calcium) | 10.15 | 10.2 | 8.6 – 11.8 | MG/DL |
| PHOS (Phosphorus) | 4.9 | 4.17 | 2.9 – 6.6 | MG/DL |
| CRE (Creatinine) | 0.75 | 0.87 | 0.3 – 1.4 | MG/DL |
| GLU (Glucose) | 92.75 | 112 | 60 – 110 | MG/DL |
| NA+ (Sodium) | 153 | 137.67 | 138 – 160 | MMOL/L |
| K+ (Potassium) | 4.35 | 4 | 3.7 – 5.8 | MMOL/L |
| GLOB (globulin) | 1.525 | 1.7 | 2.3 – 5.2 | G/DL |

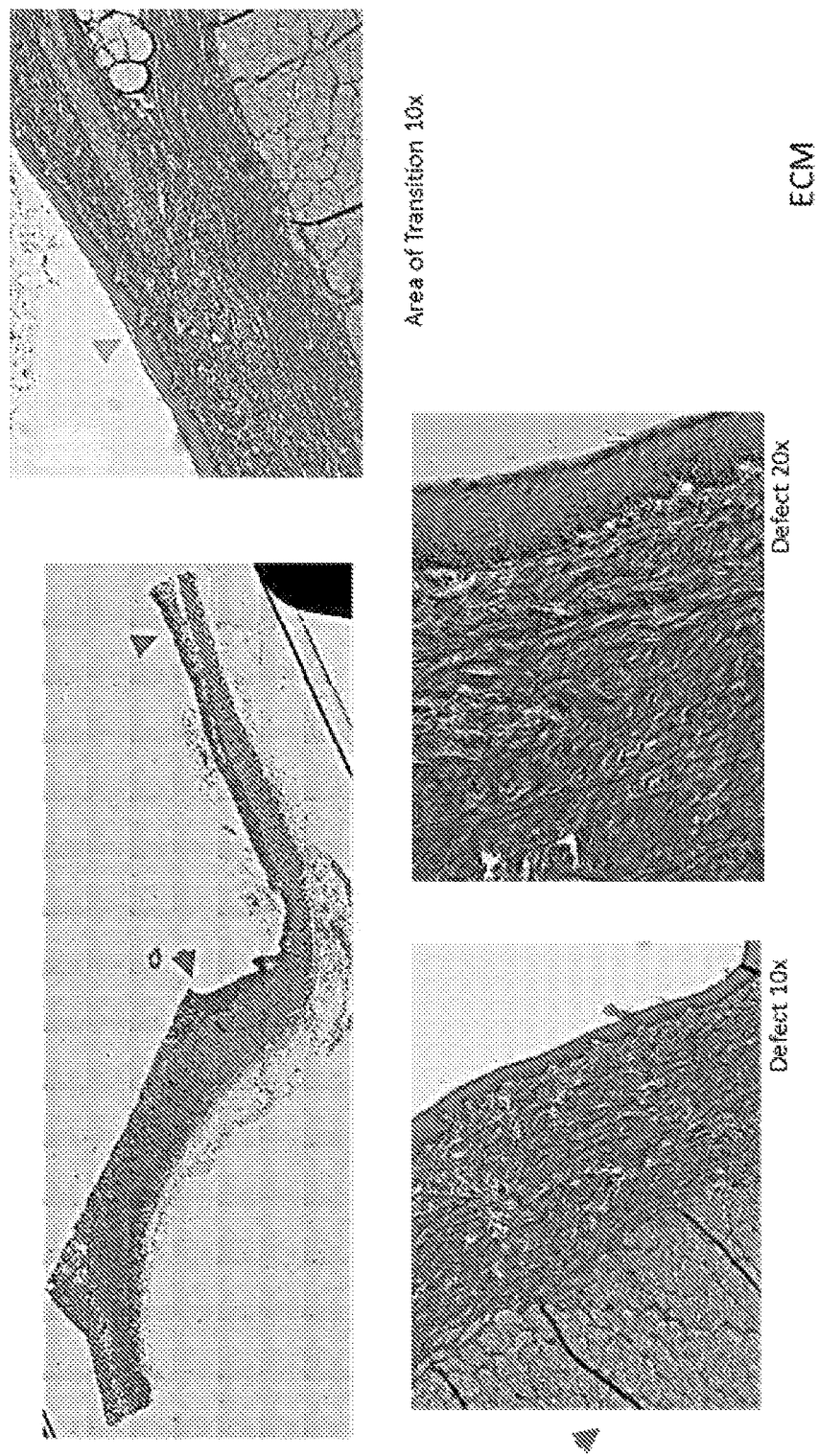
FIG. 16 Trichrome - Treatment Dog

ECM HYDROGEL FOR TREATING ESOPHAGEAL INFLAMMATION

CROSS REFERENCE TO RELATED APPLICATION

This is a § 371 U.S. national stage of International Application No. PCT/US2018/020758, filed Mar. 2, 2018, which claims the benefit of U.S. Provisional Application No. 62/465,985, filed Mar. 2, 2017, which is herein incorporated by reference in its entirety.

FIELD

This relates to the field of hydrogels, specifically to the use of an extracellular matrix (ECM) hydrogel for the treatment of esophageal inflammation such as Barrett's esophagus.

BACKGROUND

The incidence of esophageal adenocarcinoma (EAC) is rapidly rising; outpacing the rate of increase of all other cancers. Esophageal Adenocarcinoma (EAC) is associated with a dismal prognosis, with a five-year survival of less than 15%. The number of patients affected is up to 600% higher than in the 1970s' (Dubecz et al., J Gastrointest Surg. 2013 Nov. 15; Prasad et al., Amer. J. Gastroentero. 105(7): 1490-502, 2010).

Barrett's esophagus involves metaplasia of the cells of the lower (distal) portion of the esophagus, and is characterized by the replacement of the normal stratified squamous epithelium lining of the esophagus by simple columnar epithelium with goblet cells. Barrett's esophagus is strongly associated with esophageal adenocarcinoma. The main cause of Barrett's esophagus is thought to be an adaptation and response to chronic acid exposure from reflux esophagitis. The cells of Barrett's esophagus, after biopsy, are classified into four general categories: nondysplastic, low-grade dysplasia, high-grade dysplasia, and frank carcinoma. High-grade dysplasia and early stages of adenocarcinoma are usually treated by endoscopic resection and endoscopic therapies such as radiofrequency ablation, while nondysplastic and low-grade patients are generally advised to undergo annual observation with endoscopy. A need remains for methods and compositions that can be used for treating esophageal inflammation and Barrett's esophagus.

SUMMARY

Methods are disclosed for inhibiting inflammation and/or mitigating the effects of esophageal inflammation in a subject. Methods are also disclosed for reducing stricture of the esophagus. These methods include administering to the esophagus of the subject, such as a subject with esophageal inflammation or a stricture or at risk for stricture, a therapeutically effective amount of an extracellular matrix (ECM) hydrogel, wherein the ECM hydrogel has the following characteristics: a) a time to 50% gelation of less than 30 minutes at a temperature of about 37° C.; b) a flow viscosity suitable for infusion into the esophagus; and c) a stiffness of 10-600 Pascal (Pa), such as, but not limited to, 10-70 Pa. In a specific non-limiting example, the hydrogel can be an esophageal ECM hydrogel. In another specific non-limiting example, the subject can have Barrett's esophagus.

In additional embodiments, compositions are disclosed that include an esophageal extracellular matrix (ECM) hydrogel, wherein the esophageal ECM hydrogel has the following characteristics: a) a time to 50% gelation of less than ten minutes at about 37° C.; b) a flow viscosity sufficient for injection into the esophagus; and c) a stiffness of 10-70 Pascal (Pa), wherein the composition is formulated for administration to the esophagus. These compositions are of use in the methods disclosed herein.

The foregoing and other objects, features, and advantages of the invention will become more apparent from the following detailed description, which proceeds with reference to the accompanying figures.

BRIEF DESCRIPTION OF THE DRAWINGS

FIG. 3. Esophageal ECM gelation time.
FIGS. 4A-4C. Viscosity profiles are tissue-specific.
FIGS. 5A-5C. Gel stiffness is tissue-specific.
FIG. 7. ECM hydrogels promote secretion of anti-inflammatory cytokines.
FIGS. 8A-8B. ECM promotes the chemotaxis of epithelial and stem cells.
FIG. 9. Dynamic reciprocity in clinical treatment of EAC.
FIGS. 12A-12B. Evaluation of safety of eECM hydrogel.
FIG. 16. Histological analysis, dog treated with ECM hydrogel.

DETAILED DESCRIPTION

Figure 1:
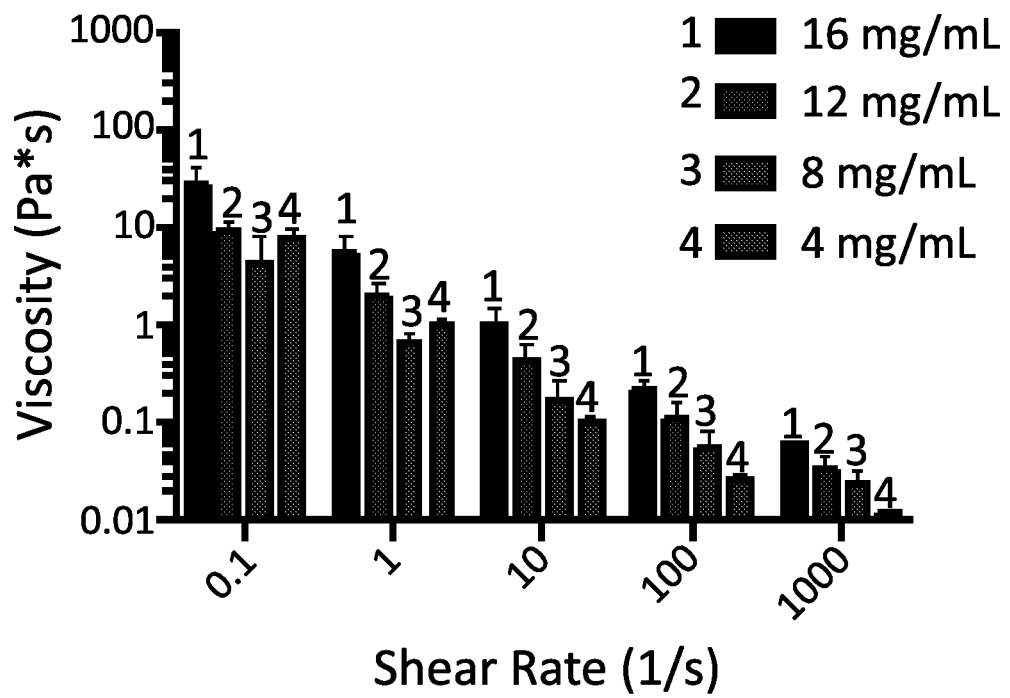
FIG. 1. Esophageal ECM Hydrogel Viscosity Profile.

When manufactured as a hydrogel, extracellular-matrix (ECM) bioscaffolds have bioactivity (Freytes et al., Biomaterials 29: 1630-7, 2008). However, ECM hydrogel has unique physical and mechanical properties. These distinctive properties extend the applications of ECM beyond those possible for the sheet form. The ECM hydrogel, in comparison to the sheet form, can be delivered to irregularly-shaped and sized surface areas, ensures contact of ECM with tissue that has an irregular topology, does not require a fixation device (e.g. sutures, stent) and does not impart adverse rigidity to the area where it is implanted. The hydrogel has the characteristic of being a liquid at room temperature (pre-gel), but becomes a gel when exposed to body temperature (37° C.), making it easily deliverable through devices like syringes, catheters, irrigators, and probes, among others.

ECM in sheet form has been used to treat late stage esophageal dysplastic and neoplastic disease, however, the need for a fixation device (i.e. stent), rigidity of the sheet form and relative invasiveness of implantation has not allowed it to expand its use. The distinctive properties of the ECM hydrogel make it ideal for application to a surface of the esophagus, and/or the treatment of esophageal disease that is not treatable with the sheet form. The ECM hydrogel's viscoelastic and mucoadhesion properties support its potential for the treatment of esophageal disease. In addition, the hydrogel can be used to reverse cancerous and pre-cancerous lesions in the esophagus.

Recently, the sheet form has been used for treatment of esophageal late stage cancerous and precancerous disease with success. For esophageal use the sheet is placed circumferentially and held in place by a stent. There are limitations to the use of a sheet form such as the need for fixation devices (i.e. sutures or stents), its inability to fill irregularly sized defects and its limited area of coverage (to the size of the sheet). In the esophagus, these limitations have constrained the use of the ECM sheet to the treatment of late stage esophageal disease, one of the few situations where the use of a temporary stent and an advanced procedure is justified.

The disclosed hydrogels can be administered topically to the esophagus. The hydrogel can be administered to the lumen of the esophagus to coat the surface. This is a non-invasive application. In some embodiments, the application is oral, such as by swallowing. In other embodiments, application can be gavage. The hydrogel is formed at the surface of the esophageal tissue. In some embodiments, the hydrogel coats the mucosa, and does not invade into the underlying submucosa or musculature.

It is disclosed herein that a hydrogel, such as a hydrogel produced from esophageal ECM, can be used to treat Barrett's esophagus, and inhibit the development of adenocarcinoma. The ECM hydrogel can inhibit inflammation and mitigate the effects of inflammation. The ECM hydrogel can reduce stricture. In some embodiments, the ECM hydrogel is effective when utilized at concentrations of about 2 mg/ml to about 20 mg/ml, such as about 8 mg/ml to about 12 mg/ml.

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Acid Protease: An enzyme that cleaves peptide bonds, wherein the enzyme has increased activity of cleaving peptide bonds in an acidic pH. For example and without limitation, acid proteases can include pepsin and trypsin.

Barrett's Esophagus: An abnormal change (metaplasia or dysplasia) in the cells of the lower (distal) portion of the esophagus. Barrett's esophagus is the diagnosis when the normal stratified squamous epithelium lining of the esophagus is replaced by simple columnar epithelium with goblet cells. Barrett's esophagus is found in 5-15% of patients who seek medical care for gastroesophageal reflux disease (GERD), although a large subgroup of patients with Barrett esophagus do not have symptoms. Barrett's esophagus is strongly associated with esophageal adenocarcinoma, and is considered to be a premalignant condition. The main cause of Barrett's esophagus is thought to be an adaptation to chronic acid exposure from reflux esophagitis. The cells of Barrett's esophagus, after biopsy, are classified into four general categories: non-dysplastic, low-grade dysplasia, high-grade dysplasia, and frank carcinoma.

Base: A compound or a solution of a compound with a pH greater than 7. For example and without limitation, the base is an alkaline hydroxide or an aqueous solution of an alkaline hydroxide. In certain embodiments, the base is NaOH or NaOH in PBS.

Comminute (comminution and comminuting): The process of reducing larger particles into smaller particles, including, without limitation, by grinding, blending, shredding, slicing, milling, cutting, shredding. ECM can be comminuted while in any form, including, but not limited to, hydrated forms, frozen, air-dried, lyophilized, powdered, sheet-form.

Diagnosis: The process of identifying a disease by its signs, symptoms and results of various tests. The conclusion reached through that process is also called "a diagnosis." Forms of testing commonly performed include blood tests, medical imaging, and biopsy.

Extracellular Matrix (ECM): The non-cellular component of tissues and organs. Natural ECMs (ECMs found in multicellular organisms, such as mammals and humans) are complex mixtures of structural and non-structural biomolecules, including, but not limited to, collagens, elastins, laminins, glycosaminoglycans, proteoglycans, antimicrobials, chemoattractants, cytokines, and growth factors. In mammals, ECM often comprises about 90% collagen by dry weight mass, in its various forms. Biologic scaffolds can be created by removing the cells from a given tissue or organ. The composition and structure of ECMs vary depending on the source of the tissue. For example, small intestine submucosa (SIS), urinary bladder matrix (UBM), esophagus (E) and liver stroma ECM each differ in their overall structure and composition due to the unique cellular niche needed for each tissue. An intact "extracellular matrix" and "intact ECM" bioscaffold consists of extracellular matrix that ideally retains activity of its structural and non-structural biomolecules, including, but not limited to, collagens, elastins, laminins, glycosaminoglycans, proteoglycans, antimicrobials, chemoattractants, cytokines, and growth factors, such as, without limitation comminuted ECM as described herein.

The activity of the biomolecules within the ECM can be removed chemically or mechanically, for example, by chemical or enzymatic cross-linking and/or by dialyzing the ECM. Intact ECM essentially has not been enzymatically digested, cross-linked and/or dialyzed, meaning that the ECM has not been subjected to a digestion, dialysis and/or a cross-linking; process, or conditions other than processes that occur naturally during storage and handling of ECM prior to solubilization. Thus, ECM that is substantially cross-linked and/or dialyzed (in anything but a trivial manner which does not substantially affect the gelation and functional characteristics of the ECM in its uses described herein) is not considered to be "intact."

Esophagogastroduodenoscopy (EGD) or Upper Gastrointestinal Endoscopy: A diagnostic endoscopic procedure that visualizes any upper part of the gastrointestinal tract up to the duodenum. An "esophageal endoscopy" is any endoscopic procedure that visualizes the esophagus. An esophageal endoscopy may sometimes be performed as part of an EGD or upper gastrointestinal endoscopy. The terms are not mutually exclusive unless expressly stated to be so.

Gelation: The formation of a gel from a sol.

Gastroesophageal Reflux Disease (GERD): A chronic symptom of mucosal damage caused by stomach acid refluxing from the stomach into the esophagus. GERD is usually caused by changes in the barrier between the stomach and the esophagus, including abnormal relaxation of the lower esophageal sphincter, which normally holds the top (proximal portion) of the stomach closed, impaired expulsion of gastric reflux from the esophagus, or a hiatal hernia. These changes may be permanent or temporary.

Flow Viscosity: A measure of the resistance of a fluid to gradual deformation by shear stress or tensile stress. Viscosity is a property of a fluid which opposes the relative motion between the two surfaces of the fluid in a fluid that are moving at different velocities. When a fluid is forced through a tube, particles that compose the fluid generally move more quickly near the tube's axis and more slowly near its walls. Stress (such as a pressure difference between the two ends of the tube) is needed to overcome the friction between particle layers to keep the fluid moving. For a given velocity pattern, the stress required is proportional to the fluid's viscosity. Viscosity is measured with viscometers and rheometers. Viscosity can be measured as pascal second (Pa*s). Water at 20° C. has a viscosity of 1.002 mPa*s.

Hydrogel: A network of polymer chains that are hydrophilic, sometimes found as a colloidal gel in which water is the dispersion medium. Hydrogels are highly absorbent natural or synthetic polymeric networks. Hydrogels also possess a degree of flexibility similar to natural tissue.

Inflammation: A localized response elicited by injury to tissue. Inflammation is characterized by the appearance in or migration into any tissue space, unit or region of any class of leukocyte in numbers that exceed the number of such cells found within such region of tissue under normal (healthy) circumstances. Inflammation is orchestrated by a complex biological response of vascular tissues to harmful stimuli, such as pathogens, damaged cells, or irritants.

Isotonic Buffered Solution: A solution that is buffered to a between 7.2 and 7.8 and that has a balanced concentration of salts to promote an isotonic environment.

Low Grade Dysplasia and High Grade Dysplasia (of the Esophagus): Pathological conditions of the esophagus. Generally, in esophageal dysplasia there is an absence of apical mucin in the internal lining of the esophagus. Frequently, both an absence of goblet cells and mucin depletion in the non-goblet columnar cells are seen in dysplastic epithelium. At low power, these areas appear more hyperchromatic as compared to uninvolved areas.

For high grade dysplasia, distortion of glandular architecture of the esophagus is usually present and may be marked; it is composed of branching and lateral budding of crypts, a villiform configuration of the mucosal surface, or intraglandular bridging of epithelium to form a cribriform pattern of "back-to-back" glands. There is dysplastic epithelium on the mucosal surface with loss of nuclear polarity, characterized by "rounding up" of the nuclei, and absence of a consistent relationship of nuclei to each other.

Preventing or treating: Inhibiting a disease refers to inhibiting the partial or full development of a disease, for example in a person who is at risk for a disease such as one caused by inflammation. An example of a person at risk for esophageal adenocarcinoma is someone with Barrett's esophagus or GERD. Inhibiting a disease process includes preventing the development of the disease. "Treatment" refers to a therapeutic intervention that ameliorates a sign or symptom of a disease or pathological condition, such as after it has begun to develop.

Sheer Stress: The component of stress coplanar with a material cross section. Shear stress arises from the force vector component parallel to the cross section. The formula to calculate average shear stress is force per unit area $$\tau = \frac{F}{A},$$

where $\tau$=the shear stress, F=the force applied, A=the cross-sectional area of material with area parallel to the applied force vector.

Stricture: A narrowing or tightening of the esophagus that causes swallowing difficulties. Symptoms of esophageal strictures include heartburn, bitter or acid taste in the mouth, choking, coughing, shortness of breath, frequent burping or hiccups, pain or trouble swallowing, vomiting blood and/or weight loss. Stricture of the esophagus can be caused by gastroesophageal reflux disease, esophagitis, a dysfunctional lower esophageal sphincter, disordered motility, lye ingestion, or a hiatal hernia. Strictures can form after esophageal surgery and other treatments such as laser therapy or photodynamic therapy. While the area heals, a scar forms, causing the tissue to pull and tighten, leading to difficulty in swallowing. Stricture can be a result of inflammation. A barium swallow test or an upper gastrointestinal endoscopy can be used to diagnose esophageal stricture.

Stiffness: The rigidity of an object or fluid. The stiffness of the extracellular matrix is important for guiding the migration of cells in durotaxis. Stiffness can be measure in Pascal (Pa), which are one newton per square meter.

Therapeutic agent: Used in a generic sense, it includes treating agents, prophylactic agents, and replacement agents. "Treatment" or "treating" means providing a substance, such as a ECM hydrogel, to a patient in an amount sufficient to measurably reduce, inhibit, or mitigate any disease symptom, slow disease progression, or cause disease regression. In certain embodiments treatment of the disease may be commenced before the patient presents symptoms of the disease. The disclosed methods inhibit esophageal inflammation and/or mitigate the effects of esophageal inflammation.

Therapeutically effective amount: A "therapeutically effective amount" of a composition, such as an ECM hydrogel, means an amount effective, when administered to a patient, to provide a therapeutic benefit such as an amelioration of symptoms, reduced decrease progression, or cause disease regression. A quantity of a specified ECM hydrogel is sufficient to achieve a desired effect in a subject being treated, such as to inhibit inflammation and/or mitigate the effects of such inflammation, such as stricture. A therapeutically effective amount can be administered systemically or locally, such as to the esophagus. In addition, an effective amount of a ECM hydrogel can be administered in a single dose, or in several doses over time. However, the effective amount will be dependent on the preparation applied, the subject being treated, the severity and type of the affliction, and the manner of administration of the compound. The ECM hydrogels of use in the methods disclosed herein have applications in both medical and veterinary settings. Therefore, the general term "subject" or "patient" is understood to include all animals, including, but not limited to, humans or veterinary subjects, such as other primates, dogs, cats, horses, and cows.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The term "about" indicates within 5 percent. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Extracellular Matrix (ECM) Hydrogels

Methods of preparing ECM hydrogels, are disclosed for example, in U.S. Pat. No. 8,361,503. Any type of extracellular matrix tissue can be used to produce a hydrogel which can be used in the methods as disclosed herein (see U.S. Pat. Nos. 4,902,508; 4,956,178; 5,281,422; 5,352,463; 5,372,821; 5,554,389; 5,573,784; 5,645,860; 5,771,969; 5,753,267; 5,762,966; 5,866,414; 6,099,567; 6,485,723; 6,576,265; 6,579,538; 6,696,270; 6,783,776; 6,793,939; 6,849,273; 6,852,339; 6,861,074; 6,887,495; 6,890,562; 6,890,563; 6,890.564; and 6,893,666 related to ECM). In certain embodiments, the ECM is isolated from a vertebrate animal, for example and without limitation, from a warm blooded mammalian vertebrate animal including, but not limited to, humans, monkeys, horses, pigs, cows and sheep. In specific non-limiting examples, the ECM is porcine or human.

The ECM can be derived from any organ or tissue, including without limitation, urinary bladder, intestine, liver, esophagus and dermis. In one embodiment, the ECM is isolated from a urinary bladder. In another embodiment, the ECM is from an esophagus. The ECM may or may not include the basement membrane portion of the ECM. In certain embodiments, the ECM includes at least a portion of the basement membrane. In other embodiments, the ECM is harvested from a cell culture. The ECM hydrogel can be produced by a combination of two or more tissue sources.

As disclosed in U.S. Pat. No. 8,361,503 (incorporated herein by reference), a urinary bladder ECM, such as porcine bladder ECM is prepared by abrading bladder tissue to remove the outer (abluminal) layers including both the tunica serosa and the tunica muscularis using a longitudinal wiping motion with a scalpel handle and moistened gauze. Following eversion of the tissue segment, the luminal portion of the tunica mucosa is delaminated from the underlying tissue using the same wiping motion. In some embodiments, perforation of the submucosa is prevented. After these tissues are removed, the resulting ECM consists mainly of the tunica submucosa. The production of hydrogels from decellularized dermal ECM is disclosed in Wolf et al., Biomaterials 33: 7028-7038, 2012, incorporated herein by reference. The production of ECM from esophageal tissue is disclosed, for example, in Badylak et al. J Pediatr Surg. 35(7):1097-103, 2000 and Badylak et al., J Surg Res. 2005 September; 128(1):87-97, 2005, both incorporated herein by reference. U.S. Pat. No. 6,893,666, incorporated herein by reference, discloses production of ECM from urinary bladder, skin, esophagus and small intestine.

Commercially available ECM preparations can also be used in the methods, devices and compositions described herein. In one embodiment, the ECM is derived from small intestinal submucosa or SIS. Commercially available preparations include, but are not limited to, SURGISIS™, SURGISIS-ES™, STRATASIS™, and STRATASIS-ES™ (Cook Urological Inc.; Indianapolis, Ind.) and GRAFTPATCH™ (Organogenesis Inc.; Canton, Mass.). In another embodiment, the ECM is derived from dermis. Commercially available preparations include, but are not limited to PELVICOL™ (sold as PERMACOL™ in Europe; Bard, Covington, Ga.), REPLIFORM™ (Microvasive; Boston, Mass.) and ALLODERM™ (LifeCell; Branchburg, N.J.). In another embodiment, the ECM is derived from urinary bladder. Commercially available preparations include, but are not limited to UBM (Acell Corporation; Jessup, Md.).

Source tissue used for preparation of ECM can be harvested in a large variety of ways and once harvested, a variety of portions of the harvested tissue may be used. ECM has also been prepared from the esophagus and small intestine, and hydrogels have been prepared from this ECM, see, for example, Keane et al., Tissue Eng. Part A, 21(17-18): 2293-2300, 2015, incorporated herein by reference. Esophageal ECM can be prepared by mechanically separating the mucosa and submucosa from the muscularis externa and digesting the mucosal layers in a buffer including trypsin, followed by exposure to sucrose, TRITON-X100®, deoxycholic acid, peracetic acid and DNAse. Small intestinal submucosa (SIS) can be prepared by mechanically removing the superficial layers of the tunica mucosa, tunica serosa, and tunica muscularis externa from the intact small intestine, leaving the submucosa, muscularis mucosa, and basilar stratum compactum intact. The SIS is then treated with peracetic acid. Exemplary protocols are provided in Keane et al.

In one embodiment, the ECM is isolated from harvested porcine urinary bladder to prepare urinary bladder matrix (UBM). Excess connective tissue and residual urine are removed from the urinary bladder. The tunica serosa, tunica muscularis externa, tunica submucosa and most of the muscularis mucosa can be removed by mechanical abrasion or by a combination of enzymatic treatment, hydration, and abrasion. Mechanical removal of these tissues can be accomplished by abrasion using a longitudinal wiping motion to remove the outer layers (particularly the abluminal smooth muscle layers) and even the luminal portions of the tunica mucosa (epithelial layers). Mechanical removal of these tissues is accomplished by removal of mesenteric tissues with, for example, Adson-Brown forceps and Metzenbaum scissors and wiping away the tunica muscularis and tunica submucosa using a longitudinal wiping motion with a scalpel handle or other rigid object wrapped in moistened gauze. The epithelial cells of the tunica mucosa can also be dissociated by soaking the tissue in a de-epithetializing solution, for example and without limitation, hypertonic saline. The resulting UBM comprises basement membrane of the tunica mucosa and the adjacent tunica propria, which is further treated with peracetic acid, lyophilized and powdered, see U.S. Pat. No. 8,361,503.

In some embodiments, the epithelial cells can be delaminated first by first soaking the tissue in a de-epithelializing solution such as hypertonic saline, for example and without limitation, 1.0 N saline, for periods of time ranging from 10 minutes to 4 hours. Exposure to hypertonic saline solution effectively removes the epithelial cells from the underlying basement membrane. The tissue remaining after the initial delamination procedure includes epithelial basement membrane and the tissue layers abluminal to the epithelial basement membrane. This tissue is next subjected to further treatment to remove the majority of abluminal tissues but not the epithelial basement membrane. The outer serosal, adventitial, smooth muscle tissues, tunica submucosa and most of the muscularis mucosa are removed from the remaining de-epithelialized tissue by mechanical abrasion or by a combination of enzymatic treatment, hydration, and abrasion.

ECM can be sterilized by any number of standard techniques, including, but not limited to, exposure to peracetic acid, low dose gamma radiation, gas plasma sterilization, ethylene oxide treatment, supercritical $CO_2$, or electron beam treatment. More typically, sterilization of ECM is obtained by soaking in 0.1% (v/v) peracetic acid, 4% (v/v) ethanol, and 95.9% (v/v) sterile water for two hours. The peracetic acid residue is removed by washing twice for 15 minutes with PBS (pH=7.4) and twice for 15 minutes with sterile water. ECM material can be sterilized by propylene oxide or ethylene oxide treatment, gamma irradiation treatment (0.05 to 4 mRad), gas plasma sterilization, peracetic acid sterilization, supercritical $CO_2$, or electron beam treatment. The ECM can also be sterilized by treatment with glutaraldehyde, which causes cross linking of the protein material, but this treatment substantially alters the material such that it is slowly resorbed or not resorbed at all and incites a different type of host remodeling which more closely resembles scar tissue formation or encapsulation rather than constructive remodeling. Cross-linking of the protein material can also be induced with carbodiimide or dehydrothermal or photooxidation methods. As disclosed in U.S. Pat. No. 8,361,503, ECM is disinfected by immersion in 0.1% (v/v) peracetic acid (a), 4% (v/v) ethanol, and 96% (v/v) sterile water for 2 h. The ECM material is then washed twice for 15 min with PBS (pH=7.4) and twice for 15 min with deionized water.

Following isolation of the tissue of interest, decellularization is performed by various methods, for example and without limitation, exposure to hypertonic saline, peracetic acid, TRITON-X® or other detergents. Sterilization and decellularization can be simultaneous. For example and without limitation, sterilization with peracetic acid, described above, also can serve to decellularize the ECM. Decellularized ECM can then be dried, either lyophilized (freeze-dried) or air dried. Dried ECM can be comminuted by methods including, but not limited to, tearing, milling, cutting, grinding, and shearing. The comminuted ECM can also be further processed into a powdered form by methods, for example and without limitation, such as grinding or milling in a frozen or freeze-dried state. In order to prepare solubilized ECM tissue, comminuted ECM is digested with an acid protease in an acidic solution to form a digest solution.

The digest solution of ECM typically is kept at a constant stir for a certain amount of time at room temperature. The ECM digest can be used immediately or be stored at $-20°$ C. or frozen at, for example and without limitation, $-20°$ C. or $-80°$ C.

Once the ECM is solubilized (typically substantially completely) the pH of the solution is raised to between 7.2 and 7.8, and according to one embodiment, to pH 7.4. Bases, such as bases containing hydroxyl ions, including NaOH, can be used to raise the pH of the solution. Likewise buffers, such as an isotonic buffer, including, without limitation, Phosphate Buffered Saline (PBS), can be used to bring the solution to a target pH, or to aid in maintaining the pH and ionic strength of the gel to target levels, such as physiological pH and ionic conditions. This forms a "pre-gel" solution. The neutralized digest solution (pre-gel) can be gelled at temperatures approaching $37°$ C., wherein the temperature approaches physiological temperature. The method typically does not include a dialysis step prior to gelation, yielding a more-complete ECM-like matrix that typically gels at $37°$ C. at specific rates (see below).

Thus, the ECM typically can be derived from mammalian tissue, such as, without limitation from one of urinary bladder, esophagus, or small intestine. The ECM hydrogel can be produced from two or more tissue source, such as 2, 3, or 4 tissue sources. In one non-limiting embodiment, the ECM is lyophilized and comminuted. The ECM is then solubilized with an acid protease in an acidic solution to produce digested ECM, such as esophageal ECM. The acid protease may be, without limitation, pepsin or trypsin, or a combination thereof. The ECM can then be solubilized at an acid pH suitable or optimal for the protease, such as greater than about pH 2, or between pH and 4, for example in a 0.01M HCl solution. The solution typically is solubilized for about 12 to about 48 hours, depending upon the tissue type (e.g., see examples below), with mixing (stirring, agitation, admixing, blending, rotating, tilting, etc.). ECM hydrogel is prepared by (i) comminuting an extracellular matrix, (ii) solubilizing intact, non-dialyzed or non-cross-linked extracellular matrix by digestion with an acid protease in an acidic solution to produce a digest solution, (iii) raising the pH of the digest solution to a pH between 7.2 and 7.8 to produce a neutralized digest solution (pre-gel solution), and (iv) gelling the solution at a temperature of approximately $37°$ C. within the esophagus of a subject of interest.

The ECM hydrogel, when exposed to temperatures of about $37°$ C., forms the gel. The ECM hydrogel in the "pre-gel" form can be frozen and stored at, for example and without limitation, $-20°$ C. or $-80°$ C. The ECM hydrogel in the "pre-gel" form can be stored at room temperature, such about $25°$ C. Thus, the ECM hydrogel is in the pre-gel form at below $37°$ C., such as at 25, 24, 23, 22, 21, 20, 19, 18, 17, 16, 15, 14, 13, 12, 11, 10, 9, 8, 7, 6, 5, $4°$ C. The ECM hydrogel can be frozen for storage, and thus, can be stored at below $0°$ C. As used herein, the term "pre-gel form" or "pre-gel" refers to the ECM hydrogel wherein the pH is increased, but has not gelled. For example and without limitation, an ECM hydrogel in the pre-gel form has a pH between 7.2 and 7.8. The ECM hydrogel can be delivered in a pre-gel form to a subject with esophageal inflammation, such as orally, via a catheter, or endoscopically.

The ECM hydrogel in the pre-gel form s amenable to introduction into the esophagus of a patient. Once introduced into the esophagus, which is approximately $37°$ C., the ECM hydrogel gels and coats the esophagus. Without being bound by theory, the ECM hydrogel includes many native soluble factors, such as, but not limited to, cytokines. The specific characteristics of non-dialyzed (whole ECM preparations prepared from a variety of tissues, such as the esophagus, are disclosed herein. The hydrogel gels with kinetics such that the ECM hydrogel can be administered via oral administration, endoscopic administration, or via a catheter into the esophagus, and the hydrogel subsequently gels within, and coats, the esophagus.

In some embodiments, the ECM hydrogel has the following characteristics: a) a time to 50% gelation of less than 30 minutes at a temperature of about $37°$ C.; b) a flow viscosity suitable for infusion into the esophagus; and c) a stiffness of i) about 10 to about 300 Pascal (Pa), ii) about 10 to about 450 Pa; iii) about 10 to about 600 Pa, iv) about 5 to about 1,000 Pa, v) about 10 to 1,000 Pa, or vi) about 10 to about 70 Pa.

In embodiments, the ECM hydrogel has the following characteristics: a) a time to 50% gelation of less than 30 minutes at a temperature of about $37°$ C.; b) a flow viscosity suitable for infusion into the esophagus; and c) a stiffness of about 10 to about-300 Pascal (Pa). In other embodiments, the ECM hydrogel has the following characteristics: a) a time to 50% gelation of less than 30 minutes at a temperature of about $37°$ C.; b) a flow viscosity suitable for infusion into the esophagus; and c) a stiffness of about 10 to about 450 Pascal (Pa). In other embodiments, the ECM hydrogel has the following characteristics: a) a time to 50% gelation of less than 30 minutes at a temperature of about 37° C.; b) a flow viscosity suitable for infusion into the esophagus; and c) a stiffness of about 10 to about 600 Pascal (Pa).

In other embodiments, the ECM hydrogel has the following characteristics: a) a time to 50% gelation of less than 30 minutes at a temperature of about 37° C.; b) a flow viscosity suitable for infusion into the esophagus; and c) a stiffness of about 5 to about 1,000 Pascal (Pa). In other embodiments, the ECM hydrogel has the following characteristics: a) a time to 50% gelation of less than 30 minutes at a temperature of about 37° C.; b) a flow viscosity suitable for infusion into the esophagus; and c) a stiffness of about 10 to about 1,000 Pascal (Pa). In more embodiments, the ECM hydrogel has the following characteristics: a) a time to 50% gelation of less than 30 minutes at a temperature of about 37° C.; b) a flow viscosity suitable for infusion into the esophagus; and c) a stiffness of 10-70 Pascal (Pa).

In specific non-limiting examples, the ECM hydrogel is an esophageal hydrogel. In other specific non-limiting examples, the ECM hydrogel can be produced from two or more tissue sources. In further non-limiting examples, the ECM hydrogel can be produced from urinary bladder or small intestine.

In additional specific non-limiting examples, the ECM hydrogel is produced by (a) solubilizing acellular extracellular matrix (ECM) by digestion of tissue with an acid protease in an acidic solution to produce digested esophageal ECM; (b) raising the pH of the digested ECM to a pH between 7.2 and 7.8 to produce a neutralized digest solution; (c) diluting the digested ECM to a concentration of about 2 mg/ml to about 16 mg/ml, such as about 8 mg/ml to about 12 mg/ml of the ECM hydrogel. This hydrogel is then introduced into the esophagus of the subject, wherein it gels. The ECM can be esophageal ECM.

The ECM hydrogels of use in the methods disclosed herein have a time to 50% gelation of less than 30 minutes at a temperature of about 37° C., such as less than 29, 28, 27, 26, 25, 24, 23, 22, 21, 20, 19, 18, 17, 16, 15, 14, 13, 12, 1, 10, 9, 8, 7, 6, 5, 4, 3 minutes. In some embodiments, the ECM hydrogels have a time to gelation of less than 10 minutes at a temperature of about 37° C. In other embodiments, the time to 50% gelation is about 3 to about 30 minutes at a temperature of about 37° C. In further embodiments, the time to 50% gelation is about 4 to about 10 minutes at a temperature of about 37° C. In yet other embodiments the time to 50% gelation is about 5 to about 10 minutes or about 10 to about 20 minutes at a temperature of about 37° C.

The disclosed ECM hydrogels can have a flow viscosity suitable for infusion into the esophagus. In some embodiments, the ECM hydrogel has a flow viscosity of about 10 to about 100 Pa*s at a sheer rate of 0.2/s, such as about 10, 20, 30, 40, 50, 60, 70, 80, or 90 Pa*s at a sheer rate of 0.2/s. In further embodiments, the ECM hydrogel has a flow viscosity of about 1 to about 40 Pa*s at a shear rate of 0.1/s, such as about 1, 2, 3, 4, 5, 6, 7, 8, 9, 10, 15, 20, 25, 30, 35, or 40 Pa*s at a shear rate of 0.1/s.

In other embodiments, the ECM hydrogel has a flow viscosity of about 0.01 to about 0.20 Pa*s at a shear rate of 1000/s, or of about 0.01 to about 0.10 Pa*s at a shear rate of 1000/s, such as about 0.01, 0.02, 0.03, 0.04, 0.05, 0.06, 0.07, 0.08, 0.09, 0.10, 0.11, 0.12, 0.13, 0.14, 0.15, 0.16, 0.17, 0.19 or 0.2 at a sheer rate of 1000/s.

In more embodiment, the ECM hydrogel has about 0.02 to about 0.8 Pa*s at a shear rate of 100/s, or of about 0.1 to about 0.8 Pa*s at a shear rate of 100/s, such as about 0.02, 0.03, 0.04, 0.05, 0.06, 0.07, 0.08, 0.09, 0.1, 0.2, 0.3, 0.4, 0.5, 0.6, 0.7, or 0.08 Pa*s.

In further embodiments, the ECM hydrogel has a flow viscosity of about 10 to about 100 Pa*s at a sheer rate of 0.2/s and a flow viscosity of about 0.01 to about 0.10 Pa*s at a sheer rate of 1000/s. In more embodiments, the ECM hydrogel has a flow viscosity of 1 to 40 Pa*s at a shear rate of 0.1/s and 0.01 to 0.2 Pa*s at a shear rate of 1000/s.

In other embodiments, the ECM hydrogel has a flow viscosity of about 1 to about 40 Pa*s, such as 1 to about 30 Pa*s, or 1 to about 20 Pa*s, or 1 to about 10 Pa*s at a sheer rate of 1/s, such as about 1, 2, 3, 4, 5, 6, 7, 8, or 9 Pa*s at a sheer rate of 1/s. The shear rate can be, for example, 10, 20, 30 or 40 Pa*s at a sheer rate of 1/s. In other embodiments, the ECM hydrogel has a flow viscosity of about 0.05 to about 0.20 at a sheer rate of 100/s, such as about 0.05, 0.06, 0.07, 0.08, 0.09, 0.1, 0.15 or 0.2 at a sheer rate of 100/s. the flow viscosity is about 0.1 to about 25 Pa*s at a shear rate of 1/s, and is about 0.02 to about 0.8 Pa*s at a shear rate of 100/s. In additional embodiments, the flow viscosity is about 1 to about 10 Pa*s at a shear rate of 1/s, and is about 0.05 to about 0.20 at a shear rate of 100/s.

In further embodiments, the ECM hydrogel has a flow viscosity of about 10 to about 100 Pa*s at a sheer rate of 0.2/s. In other embodiments, the ECM hydrogel has a flow viscosity of about 0.01 to about 0.10 Pa*s at a sheer rate of 1000/s. In other embodiments, the ECM hydrogel has a flow viscosity of about 1 to about 40 Pa*s at a shear rate of 0.1/s and is 0.01 to 0.2 Pa*s at a shear rate of 1000/s.

The disclosed ECM hydrogels have a stiffness i) about 10 to about 300 Pascal (Pa), ii) about 10 to about 600 Pa, iii) about 5 to about 1,000 Pa, iv) about 10 to 1,000 Pa, or v) about 10 to about 70 Pa. The ECM hydrogel can have a stiffness of about 10 to about 300 Pascal (Pa), such as about 10 to about 70 Pa, about 10 to about 100 Pascal (Pa), or about 10 to about 150 Pa, about 10 to about 200 Pa, or about 10 to about 250 Pa. In some embodiments, the disclosed ECM hydrogels have a stiffness of about 10, 15, 20, 25, 30, 35, 40, 45, 50, 55, 60, 65, or 70 Pa. In other embodiments, the disclosed ECM hydrogels have a stiffness of about 10 to about 80, 90, 100, 110, 120, 130, 140, 150, 160, 170, 180, 190, 200, 210, 220, 230, 240, 250, 260, 270, 280, 290, or 300 Pa. In further embodiments, the disclosed ECM hydrogel can have a stiffness of about 70, 75, 80, 85, 90, 95, 100, 110, 120, 130, 140, 150, 160, 170, 180, 190, 200, 210, 220, 230, 240, 250, 260, 270, 280, 290, or 300 Pa.

In some embodiments, the ECM concentration in the hydrogel is about 2 mg/ml to about 20 mg/ml, such as about 8 mg/ml to about 12 mg/ml or about 2 mg/ml to about 16 mg/ml. In other embodiments, the ECM concentration in the hydrogel is about 2, 3, 4, 5, 6, 7, 8, 9, 10, 11, 12, 13, 14, 15, or 16 mg/ml. Exemplary concentrations of use include, but are not limited to, about 9 mg/ml to about 11 mg/ml, and about 10/mg to about 12 mg/ml. Additional exemplary concentrations include about 8 mg/ml to about 10 mg/ml, about 8 mg/ml to about 11 mg/ml, about 8 mg/ml o about 13 mg/ml, about 8 mg/ml to about 14 mg/ml, about 8 mg/ml to about 15 mg/ml, and about 8 mg/ml to about 16 mg/ml. Further exemplary concentrations of use also include about 6 mg/ml to about 12 mg/ml, about 13 mg/ml, about 14 mg/ml, about 15 mg/ml or about 16 mg/ml.

The disclosed ECM hydrogels can be provided as components of a kit. The ECM hydrogel can be provided in frozen or lyophilized form. In some embodiments, the kit can include the components needed to form the hydrogel, such as one container including the hydrogel, such as in a lyophilized form, one container including a solution for solubilizing the lyophilized hydrogel, and optionally a container comprising a neutralizing solution for neutralizing the solubilized form. In other embodiments, the kit can include a container including the solubilized hydrogel, and a second container including a neutralizing agent.

Optionally, such a kit includes additional components including packaging, instructions and various other reagents, such as buffers, substrates, or other therapeutic ingredients. The kit can include a container and a label or package insert on or associated with the container. Suitable containers include, for example, bottles, vials, syringes, etc. The containers may be formed from a variety of materials such as glass or plastic. The container typically holds a composition including the ECM hydrogel, such as in frozen or lyophilized form, which is effective for inhibiting esophageal inflammation and/or mitigating the effects of esophageal inflammation in a subject. In several embodiments, the container may have a sterile access port (for example the container may be an intravenous solution bag or a vial having a stopper pierceable by a hypodermic injection needle). The label or package insert indicates that the composition is used for treating the particular condition, such as Barrett's esophagus.

The label or package insert typically will further include instructions for use. The package insert typically includes instructions customarily included in commercial packages of therapeutic products that contain information about the indications, usage, dosage, administration, contraindications and/or warnings concerning the use of such therapeutic products. The instructional materials may be written, in an electronic form (such as a computer diskette or compact disk) or may be visual (such as video files). The kits may also include additional components to facilitate the particular application for which the kit is designed, such as needles or catheters. The kits may additionally include buffers and other reagents routinely used for the practice of a particular method. Kits and appropriate contents are well known to those of skill in the art.

Methods of Treatment

Methods are disclosed herein for treating esophageal inflammation. Methods are also disclosed for reducing stricture of the esophagus. Without being bound by theory, an ECM hydrogel allows treatment of early stage neoplastic esophageal disease and dysplastic esophageal disease. The disclosed hydrogels can be used to treat both pre-neoplastic and neoplastic esophageal diseases. The versatility of the disclosed hydrogels allow them to be used to treat esophageal burns, ulcerations and other pathologies which can extend throughout multiple, non-connected areas of the esophagus. The disclosed hydrogels are also of use for treatment of long segment or disperse esophageal injuries without the need for the use of stent or invasive techniques. It is not feasible to use the sheet form of ECM in these conditions, because multiple stents and ECM sheets across the surface of the esophagus would be required. Furthermore, the sheet and hydrogel form of ECM have major differences in terms of active components. Any of the disclosed hydrogels are of use in these methods of treatment. One of skill in the art, such as a skilled physician, can readily identify therapeutic efficacy.

Thus, a subject can be selected that has esophageal inflammation. A subject can has be selected that has, or is at risk for having structure of the esophagus.

In some embodiments, the subject is apparently healthy, such as a subject who does not exhibit symptoms of esophageal adenocarcinoma (EAC) (for example, does not have EAC, and/or has not previously had gastroesphogeal reflux disease (GERD) or Barrett's esophagus), but has esophageal inflammation. In some examples, a healthy subject is one that if examined by a medical professional, would be characterized as healthy and free of symptoms, such as GERD. However, the subject has esophageal inflammation, for example as determined by endoscopic administration. In some embodiments, the disclosed methods inhibit this inflammation.

In other embodiments, the subject has GERD and/or Barrett's esophagus. In specific non-limiting examples, the subject can use acid reducing drugs such as proton pump inhibitors or histamine antagonists to suppress gastroesophageal discomfort. The subject may be at increased risk due to smoking and/or alcohol use. The subject can have low grade dysplasia or high grade dysplasia of the esophagus. In some embodiments, the subject does not have esophageal adenocarcinoma. However, the subject can be at risk for esophageal adenocarcinoma.

In some embodiments, the method inhibits or reverses the development of esophageal neoplasia in the subject. In other embodiments, the method restores the epithelial barrier in the esophagus of the subject. In further embodiments, the method increases chemotaxis of both epithelial cells and/or stem cells to the site of injury in the esophagus of the subject. In further embodiments, the method inhibits the development of esophageal adenocarcinoma. In other embodiments the treatment permits the subject to reduce or avoid use of proton pump inhibitors and/or histamine antagonist drugs. However, the disclosed methods can be used in conjunction with proton pump inhibitors and/or histamine antagonist drugs.

In further embodiments, treatment reduces stricture as compared to a control, such as a subject not treated with the ECM hydrogel. The treatment can increase circumference of the esophagus as compared to a control, such as a subject not treated with the ECM hydrogel.

An ECM hydrogel, as disclosed herein, is maintained at a temperature at or below which it gels, such as at or below room temperature (e.g., about 25° C.). The ECM hydrogel can be maintained, for example, at 25° C. or 4° C. prior to administration. An effective amount of the ECM hydrogel, in the pre-gel form, is then administered to the esophagus of the subject. The ECM hydrogel can be administered orally, such that the hydrogel is swallowed by the subject and gels when delivered to the esophagus. The ECM hydrogel can be administered directly to the esophagus, using either a catheter or by endoscopic administration. The ECM hydrogel gels in the esophagus of the subject, which is at a temperature of approximately 37° C. In some embodiments, about 5 to about 60 ml of the ECM hydrogel is administered to the subject, such as about 10 ml to about 30 ml of the ECM hydrogel, such as about 10, 15, 20, 25 or 20 ml of the ECM hydrogel. The ECM hydrogel can be provided in in a lyophilized or frozen form, and reconstituted just prior to administration to the subject.

The disclosed methods include administering to the esophagus of the subject, such as, but not limited to, a subject with esophageal inflammation, or a subject with stricture or at risk for structure, a therapeutically effective amount of an ECM hydrogel as disclosed herein, in the pre-gel form, and allowing the hydrogel to gel in the esophagus of the subject. In some embodiments, the ECM hydrogel a) a time to 50% gelation of less than 30 minutes at a temperature of about 37° C., b) a flow viscosity suitable for infusion into the esophagus; and c) a stiffness of 10-70 Pascal (Pa). However, any of the hydrogels disclosed above can be utilized. The ECM hydrogel can, in some embodiments, be derived from any mammalian tissue, such as but not limited to porcine or human tissue, and be, in some non-limiting examples, urinary bladder, small intestine, or the esophagus. Any of the hydrogels disclosed above can be used in for the treatment of esophageal inflammation and/or for restoring an epithelial barrier in the esophagus of a subject. Any of the hydrogels disclosed above can also be used to treat stricture. In some embodiments, local delivery to the surface avoids any undesired side effects. In specific non-limiting example, the subject has Barrett's esophagus or is at risk for having Barrett's esophagus.

The disclosed hydrogels can be administered topically to the mucosa of the esophagus in the pre-gel form. The hydrogel can be administered to the lumen of the esophagus to coat the surface, using a non-invasive method of application. In some embodiments, the application is oral, such as by swallowing the hydrogel in the pre-gel form. In other embodiments, application can be gavage, wherein the hydrogel in the pre-gel form is place at the desired location. In some embodiments, the hydrogel coats the mucosa, and does not invade into the underlying submucosa or musculature.

One of skill in the art can readily formulate the hydrogel, such that the pre-gel form can be swallowed by the subject being treated. In yet another embodiment, the hydrogel is provided in the pre-gel form via endoscopy to make sure that the medicament is locally delivered, such as specifically to the region of the esophagus that needs treatment. For example, local delivery of the hydrogel can be via an endoscope/gastroscope. Generally, delivery is topical to the mucosa of the esophagus, in order to non-invasively deliver the pre-gel form of the hydrogel. The hydrogel gels at the surface and coats the desired area of the mucosa. In some embodiments, The ECM hydrogel gels and provides a protective barrier to protect the mucosa.

In some embodiments, esophagogastroduodenoscopy (EGD) or upper gastrointestinal endoscopy can be performed for the subject of interest. These procedures can be performed before the application of the hydrogel, select the subject of interest. These procedures can also be performed following the use of the disclosed methods, to evaluate the effects on the subject, and to determine if additional applications are necessary.

Exemplary Embodiments

Clause 1. A method for inhibiting esophageal inflammation or reducing esophageal stricture in a subject, comprising administering to the esophagus of the subject with esophageal inflammation a therapeutically effective amount of an extracellular matrix (ECM) hydrogel, wherein the ECM hydrogel has the following characteristics: a) a time to 50% gelation of less than 30 minutes at a temperature of about 37° C.; b) a flow viscosity suitable for infusion into the esophagus; and c) a stiffness of i) about 10 to about 300 Pascal (Pa), ii) about 10 to about 450 Pa; iii) about 10 to about 600 Pa, iv) about 5 to about 1,000 Pa, v) about 10 to 1,000 Pa, or vi) about 10 to about 70 Pa, thereby inhibiting esophageal inflammation or reducing esophageal stricture in the subject.

Clause 2. The method of Clause 1, wherein the time to 50% gelation is about 3 to about 30 minutes at about 37° C.

Clause 3. The method of Clause 1, wherein the time to 50% gelation is about 3 to about 10 minutes at about 37° C.

Clause 4. The method of Clause 2, wherein the time to 50% gelation is about 4 to about 10 minutes.

Clause 5. The method of any one of Clauses 1-4, wherein the flow viscosity is about 1 to about 40 Pa*s at a shear rate of about 0.1/s and is about 0.01 to about 0.2 Pa*s at a shear rate of 1000/s.

Clause 6. The method of any one of Clauses 1-4, wherein the flow viscosity is about 0.1 to about 25 Pa*s at a shear rate of 1/s, and is about 0.02 to about 0.8 Pa*s at a shear rate of about 100/s.

Clause 7. The method of any one of Clauses 1-6, wherein the ECM hydrogel has a stiffness of 10-70 Pa.

Clause 8. The method of any one of Clauses 1-7, wherein the ECM hydrogel is an esophageal ECM hydrogel.

Clause 9. The method of any one of Clauses 1-8, wherein the ECM concentration in the hydrogel is 2 mg/ml to about 16 mg/ml.

Clause 10. The method of any one of Clauses 1-9, wherein the ECM hydrogel is administered orally, endoscopically or via a catheter.

Clause 11. The method of any one of Clauses 1-10, wherein the ECM hydrogel is produced by (a) solubilizing decellularized extracellular matrix (ECM) by digestion of tissue with an acid protease in an acidic solution to produce digested esophageal ECM; and (b) raising the pH of the digested esophageal ECM to a pH between 7.2 and 7.8 to produce a neutralized digest solution.

Clause 12. The method of Clause 11, wherein (b) raising the pH of the digested ECM comprises adding a base or an isotonic buffer to raise the pH of the digested ECM.

Clause 13. The method of Clause 10 or Clause 11, wherein the acid protease is pepsin, trypsin or a combination thereof.

Clause 14. The method of any one of Clauses 1-13, wherein the ECM hydrogel is maintained at or below 25° C. prior to administration to the subject.

Clause 15. The method of any one of Clauses 1-14, wherein the subject has Barrett's esophagus or is at risk of Barrett's esophagus.

Clause 16. The method of Clause 15, wherein the method inhibits the development of esophageal neoplasia in the subject.

Clause 17. The method of any one of Clauses 1-16, wherein the ECM hydrogel restores the epithelial barrier in the esophagus of the subject.

Clause 18. The method of any one of Clauses 1-17, wherein the ECM hydrogel increases chemotaxis of both epithelial cells and/or stem cells to the site of injury in the esophagus of the subject.

Clause 19. The method of any one of Clauses 1-18, wherein the ECM hydrogel reduces esophageal stricture in the subject.

Clause 20. A composition comprising an extracellular matrix (ECM) hydrogel, wherein the ECM hydrogel has the following characteristics: a) a time to 50% gelation of less than ten minutes at about 37° C.; b) a flow viscosity sufficient for injection into the esophagus; and a stiffness of i) about 10 to about 300 Pascal (Pa), ii) about 10 to about 450 Pa; iii) about 10 to about 600 Pa, iv) about 5 to about 1,000 Pa, v) about 10 to 1,000 Pa, or vi) about 10 to about 70 Pa, and wherein the composition is formulated for administration to the esophagus.

Clause 21. The composition of Clause 20, wherein the time to 50% gelation is a) about 3 to about 30 minutes; b) about 4 to about 10 minutes; or c) is about 3 to about 10 minutes, at about 37° C.

Clause 22. The composition of Clause 20 or Clause 21, wherein the hydrogel has a stiffness of about 10 to about 70 Pa.

Clause 23. The composition of any one of Clauses 20-22, comprising about 2 mg/ml to about 16 mg/ml of the ECM hydrogel.

Clause 24. The composition of any one of Clauses 21-23, wherein the ECM hydrogel is produced by: (a) solubilizing decellularized extracellular matrix (ECM) by digestion of esophageal tissue with an acid protease in an acidic solution to produce digested esophageal ECM; (b) raising the pH of the digested esophageal ECM to a pH between 7.2 and 7.8 to produce a neutralized digest solution; and (c) diluting the digested esophageal ECM to a concentration of about 8 mg/ml to about 12 mg/ml of the ECM hydrogel.

Clause 25. The composition of Clause 24, wherein (b) raising the pH of the digested ECM comprises adding a base or an isotonic buffer to raise the pH of the digested esophageal ECM Clause 26. The composition of Clause 24 or Clause 25, wherein the acid protease is pepsin, trypsin or a combination thereof.

Clause 27. The composition of any one of Clauses 20-26, wherein the ECM hydrogel is maintained at or below 25° C.

Clause 28. The composition of any one of Clauses 20-27, for use in inhibiting esophageal inflammation in a subject.

Clause 29. The composition of any one of Clauses 20-27, for use in restoring an epithelial barrier in an esophagus of a subject.

Clause 30. The composition of Clause 28 or Clause 29, wherein the subject has Barrett's esophagus.

Clause 31. The composition of any one of Clauses 20-27, for reducing esophageal stricture in a subject.

Clause 32. A kit comprising a) a container, wherein the container comprises the composition of any one of Clauses 20-31, or a lyophilized form thereof, and b) instructions for using the composition.

Clause 33. A composition for use in any one of the methods of Clauses 1-19.

The disclosure is illustrated by the following non-limiting Examples.

EXAMPLES

Mucosal inflammation, or mucositis, is an inflammatory condition characterized by swelling, irritation, and discomfort of the mucosal linings of the gastrointestinal tract. Mucositis can result in erosions or ulcers, which can be present throughout the gastrointestinal tract. As an inflammation of the mucosal lining, which often involves infection and/or ulceration, mucositis is a serious and often painful condition. It is disclosed herein that extracellular matrix (ECM) hydrogels are a potential therapeutic for treating mucosal inflammation, such as esophageal inflammation. The ECM hydrogel can provide a protective barrier from continued insult to the mucosa, promote an environment that is anti-inflammatory, and/or facilitates repair of damaged and inflamed mucosa.

Example 1

Viscoelastic Properties of Hydrogels

Rheology was performed on homologous esophageal ECM (eECM) hydrogels for a range of ECM concentrations (4-16 mg/mL). Samples were placed on a rheometer at 10° C., a temperature well below gelation, and a steady state flow test (shear rate 0.1-1000 1/s) was performed to determine the viscosity profile of the ECM pre-gels (FIG. 1).

Figure 2:
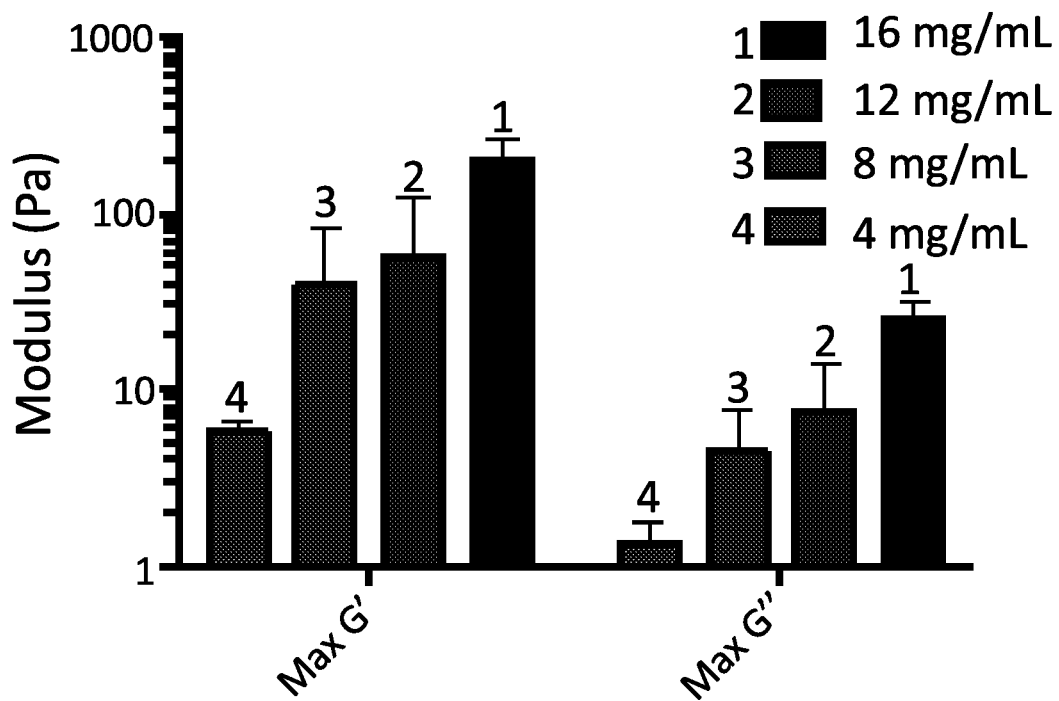
FIG. 2. Esophageal ECM hydrogel stiffness.

At each shear rate, viscosity increases with increasing ECM concentration, and the ECM pre-gels are shear-thinning (viscosity decreases with increasing shear rate). Shear-thinning is a good property for an ECM pre-gel that may be injected through a catheter where it can experience a range of shear rates of 10-1000 1/s. Further evidence of injectability was obtained in videos, which showed ECM pre-gels (Esophageal ECM and UBM, 8-12 mg/mL tested dyed in blue) are all injectable through an oral gavage (5 fr size, ~15.9 G). Temperature was then rapidly raised to 37° C. to induce gelation, and a time sweep (0.5% oscillatory strain) was performed at 37° C. to measure gel stiffness (FIG. 2) and gelation time (FIG. 3). FIG. 2 shows that the storage modulus (G') or "stiffness" of the formed ECM hydrogel increases with increasing ECM concentration. A similar trend was observed for the loss modulus (G"), or the viscous component of the formed ECM hydrogel. The time to 50% gelation was measured during the time sweep test (FIG. 3). eECM shows concentration dependent gelation times i.e., gelation time decreased with increasing ECM concentration.

Figure 4C:
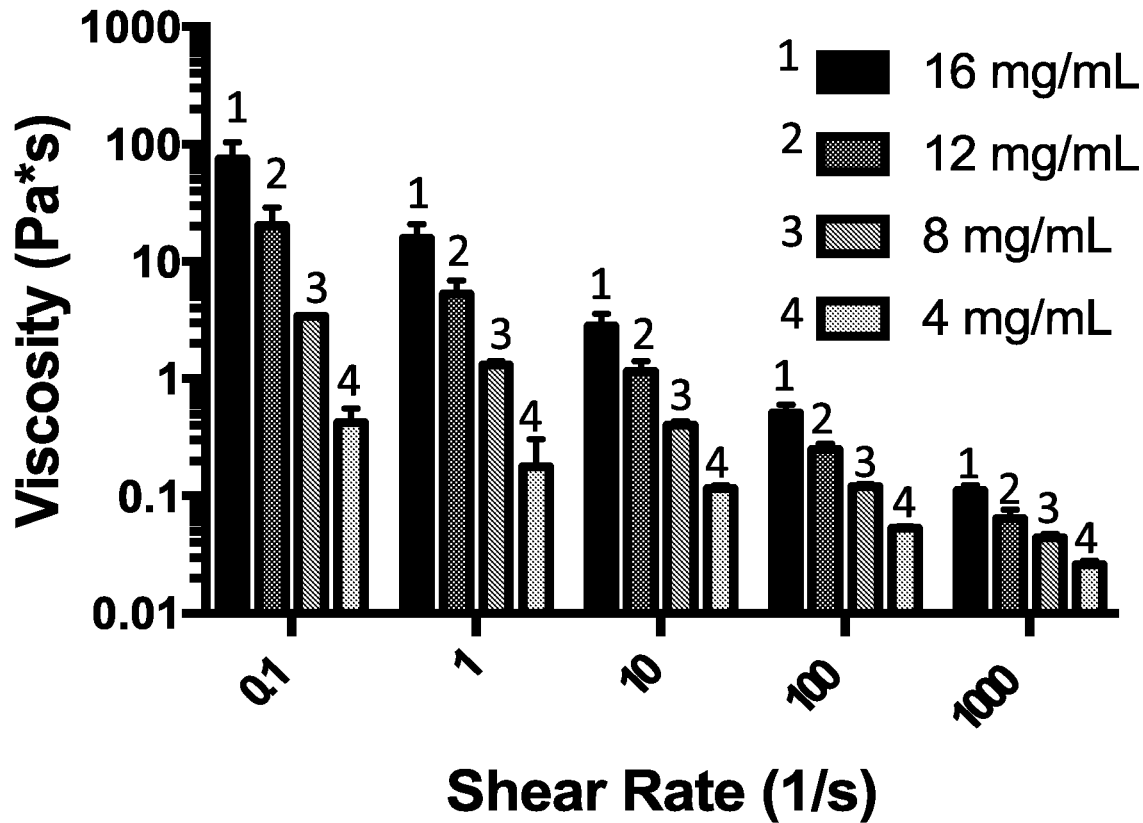

Rheology was performed on two heterologous ECM hydrogels: Urinary bladder matrix ECM (UBM) and Dermal ECM (MIRM5). Viscoelastic properties are shown in comparison to the homologous esophageal ECM hydrogel (eECM) in FIGS. 4-6.

|  | 4 mg/mL | | | 8 mg/mL | | | 12 mg/mL | | | 16 mg/mL | | |
|---|---|---|---|---|---|---|---|---|---|---|---|---|
|  | Mean (Pa) | SD (Pa) | N | Mean (Pa) | SD (Pa) | N | Mean (Pa) | SD (Pa) | N | Mean (Pa) | SD (Pa) | N |
|  | eECM | | | | | | | | | | | |
| Max G' | 5.74 | 0.73 | 3 | 39.64 | 43.18 | 3 | 56.95 | 66.72 | 3 | 205.20 | 58.98 | 3 |
|  | UBM | | | | | | | | | | | |
| Max G' | 53.49 | 5.29 | 3 | 87.36 | 18.64 | 3 | 129.70 | 16.46 | 3 | 308.63 | 91.54 | 3 |
|  | dECM | | | | | | | | | | | |
| Max G' | 0.42 | 0.57 | 3 | 3.26 | 1.17 | 3 | 35.16 | 33.44 | 3 | 59.18 | 19.64 | 3 |

A steady shear test was similarly performed as described for FIG. 1. Dermal ECM (FIG. 4B) and UBM (FIG. 4C) show a concentration-dependent increase in viscosity with increasing ECM concentration and shear-thinning profiles of the ECM hydrogels i.e., viscosity decreases with increasing shear rate for each ECM concentration. The viscosity ranges were distinctive for each tissue type.

Figure 5A:
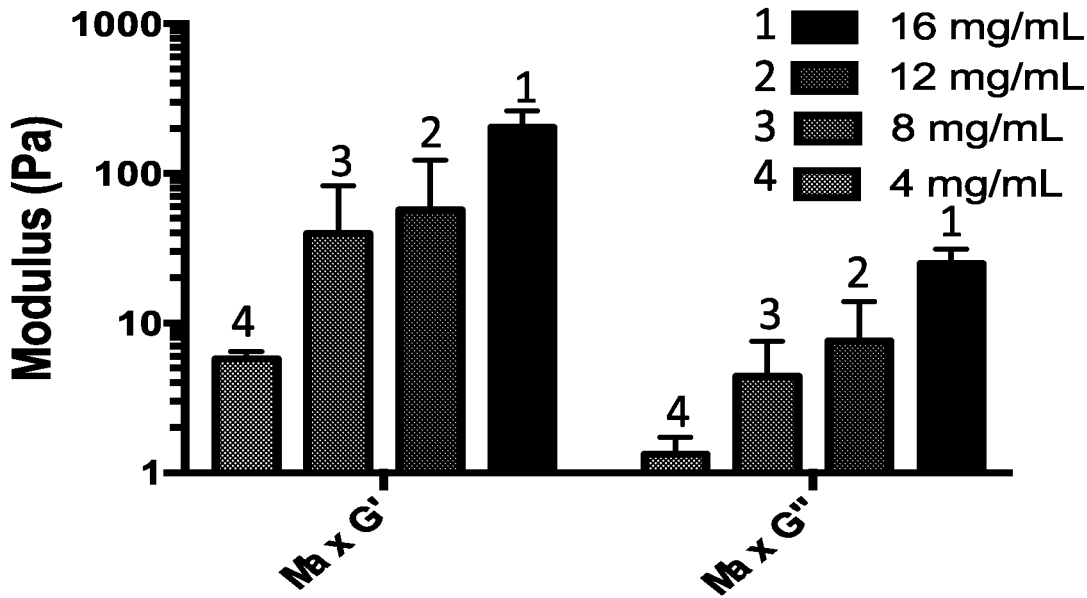
Figure 6A:
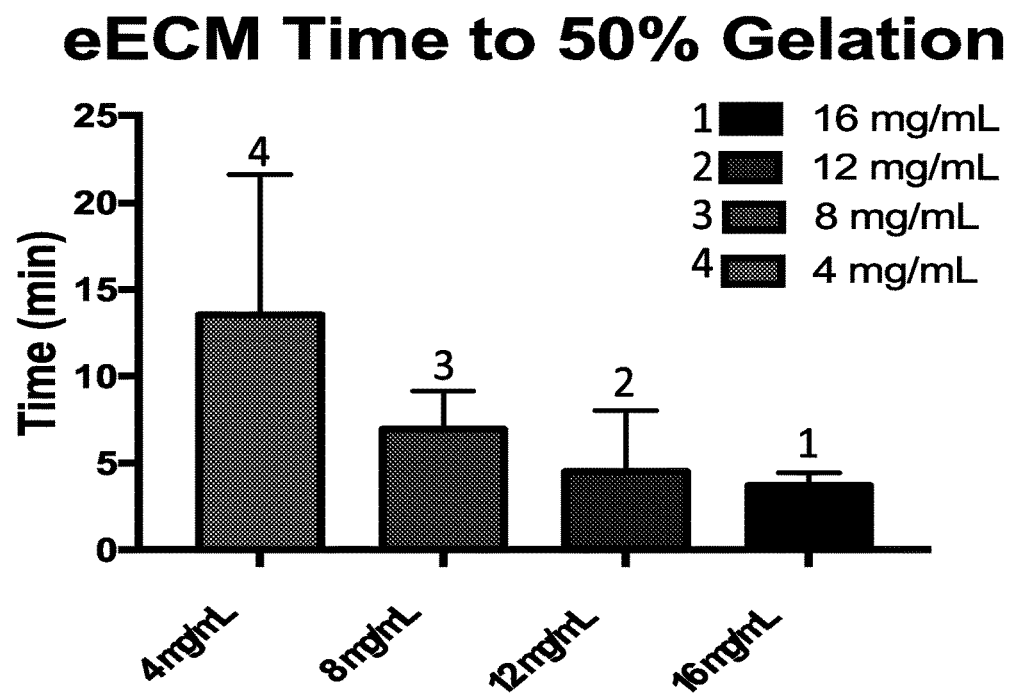
FIGS. 6A-6C. ECM gelation time is tissue-specific.
Figure 6B:
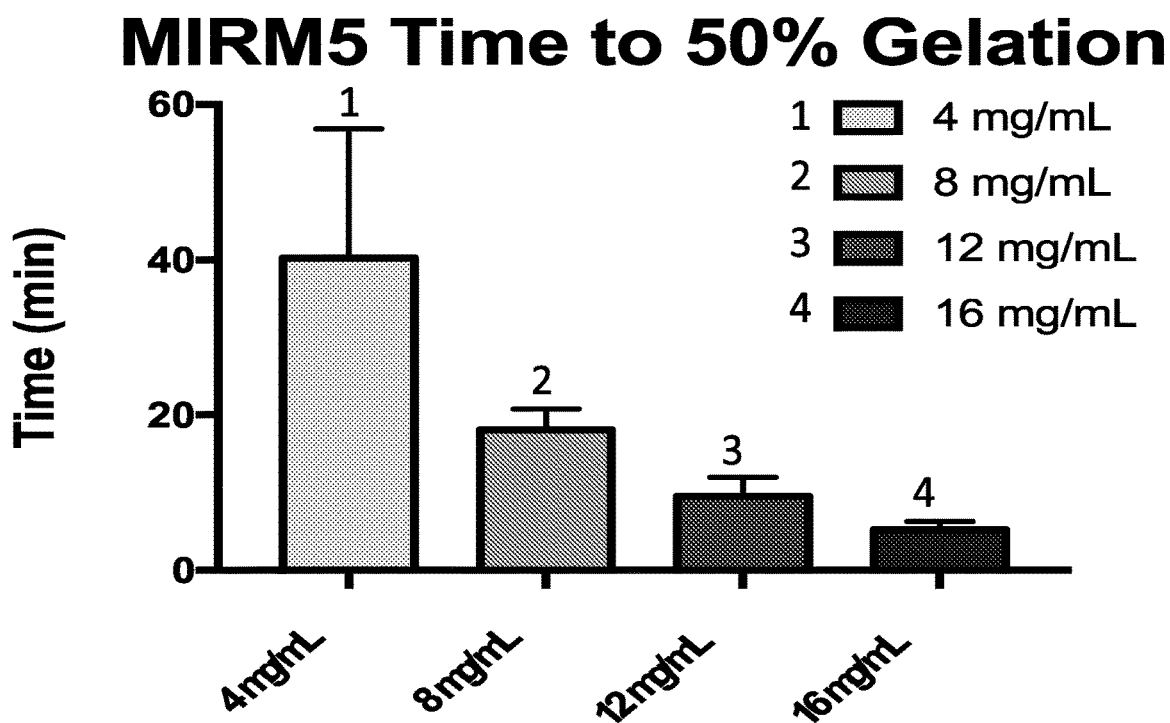

UBM ECM (FIG. 5C) showed increasing storage modulus (stiffness) with increasing ECM concentration similarly as esophageal ECM (FIG. 5A). Dermal ECM (FIG. 5B) did not form a hydrogel at the low concentration of 4 mg/mL, demonstrating that not all ECM hydrogels derived from different tissue sources behave similarly. The stiffness ranges of the three ECM hydrogels was distinctive.

Figure 6C:
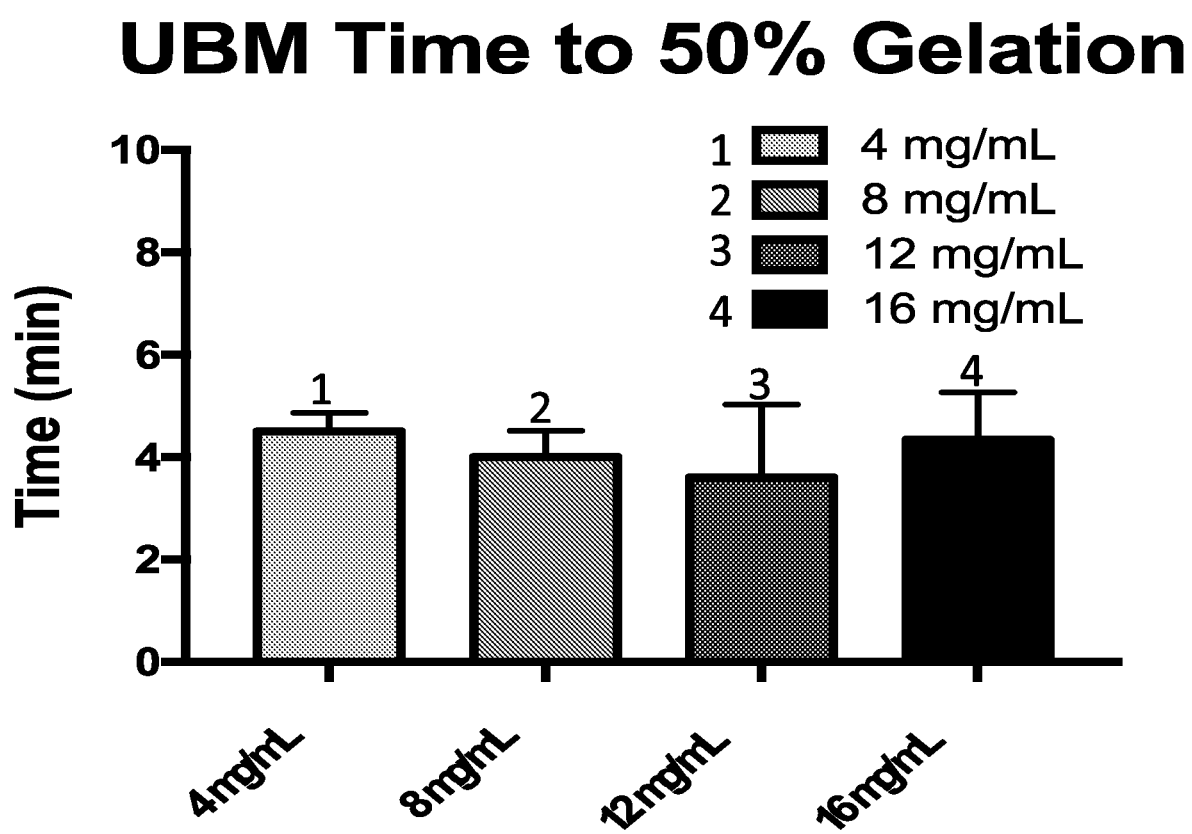

Dermal ECM (FIG. 6B) showed concentration-dependent gelation times, i.e., gelation time decreased with increasing ECM concentration, similarly to esophageal ECM (FIG. 6A), while UBM showed concentration-independent gelation times, i.e. gelation time remained constant for all ECM concentrations (FIG. 6C). The distinctive gelation profiles further demonstrate the variability of the ECM hydrogel derived from different tissue sources. Thus, esophageal hydrogels provide unique properties, and are of use at a variety of concentrations such as, but not limited to, from 8 mg/ml to about 12 mg/ml.

Example 2

Treating Mucosal Inflammation with an ECM Hydrogel

Mucosal inflammation, or mucositis, is an inflammatory condition characterized by swelling, irritation, and discomfort of the mucosal linings of the gastrointestinal tract. Mucositis can result in ulcers, which can be present throughout the gastrointestinal tract. As an inflammation of the mucosal lining, which often involves infection and/or ulceration, mucositis is a serious and often painful condition.

Mucositis often develops as a complication of chemo- or radiation therapy for cancer, for example. The goal of radiation and chemotherapy in cancer treatment—to kill rapidly dividing cancer cells—also affects epithelial cells of the mucous membranes lining regions such as the gastrointestinal tract, leading to mucositis. Exposure to radiation and/or chemotherapeutics often results in significant disruption of cellular integrity in mucosal epithelium and the underlying connective tissue, leading to inflammation, infection and/or ulceration at mucosal sites such as, for example, in the esophagus and other portions of the GI tract.

Extracellular matrix (ECM) hydrogels are a therapeutic for treating mucosal inflammation. Without being bound by theory, the mechanism by which ECM may support mucosal healing is (1) by formation of a hydrogel that provides a protective barrier from continued insult to the mucosa, (2) by promoting an environment that is anti-inflammatory, and/or (3) by facilitating repair of damaged and inflamed mucosa. The properties of esophageal hydrogels were investigated, as disclosed in Example 1.

Macrophages, when exposed to ECM hydrogels, elicit a secreted cytokine profile that is primarily anti-inflammatory, including elevated levels of PGE2 (FIG. 7). The level of anti-inflammatory cytokines varies depending upon the tissue from which the ECM was derived. Esophageal hydrogels provide strong anti-inflammatory effects.

Mucosal repair requires not only inflammation reduction but also the reestablishment of an epithelial barrier and/or a physical barrier. ECM hydrogels can promote the restoration of an epithelial barrier by increasing the chemotaxis of both epithelial cells and stem cells. The secreted products of macrophages exposed to ECM enhance the migration of epithelial cells (FIG. 8A). Furthermore, ECM hydrogels directly promote the chemotaxis of esophageal stem cells; these effects are dependent upon the source tissue from which the ECM was derived (FIG. 8B). Esophageal stem cells migrated preferentially towards esophageal ECM and small intestine ECM. FIG. 9 shows exemplary treatment of Barrett's esophagus.

Figure 10A:
FIGS. 10A-10B. Effects of hydrogel administration.
Figure 10B:

FIG. 10A shows the effects forty minutes after oral administration, the hydrogel remained coating the mucosa despite normal swallowing and could be identified. This was performed to test the mucoadhesiveness of the gel in-vivo to confirm that oral swallowing was effective. As shown in FIG. 10B, using a catheter and endoscope, the hydrogel was delivered to a specified location within the esophagus (in this case in the shape of a ring). Thus, the hydrogel was delivered to a specific topical location within the esophagus.

Figure 11:
FIG. 11. Effects of hydrogel administration after 30 days.

FIG. 11 also shows the effects of hydrogel treatment. The top row is the result of constant reflux for at least three months in the animals, with esophageal inflammation. The three dogs to the left were treated with Omeprazole (a proton pump inhibitor) and the esophageal ECM hydrogel. The last animal (right panel) was only treated with Omeprazole. After 30 days of treatment, improvement in esophageal inflammation can be seen in the three animals that received ECM hydrogel. The animal that only received Omeprazole showed no improvement (gray box, right panels).

FIGS. 12A-12B show an evaluation of the safety of the ECM hydrogel. The animals underwent a procedure that increased the acid reflux to create esophagitis, and subsequently create Barrett's Esophagus. None of the eight animals lost weight after surgery to induce BE nor during treatment with the hydrogel (FIG. 12A). Physiological parameters were analyzed. After 30 days of twice daily administration of the hydrogel, the animal's physiologic parameters were stable and did not go out of the normal range (FIG. 12B).

Figure 13B:
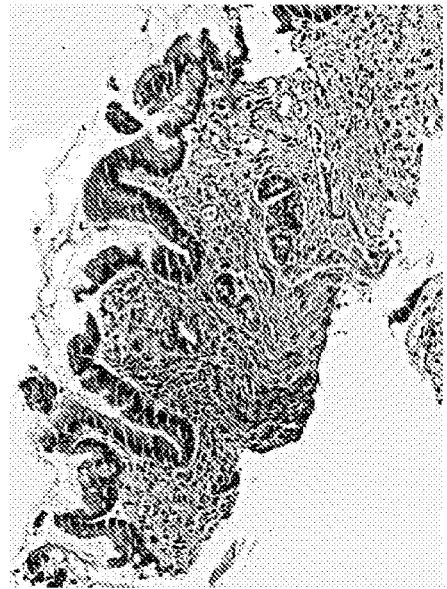
FIGS. 13A-13D. Histology.
Figure 13D:
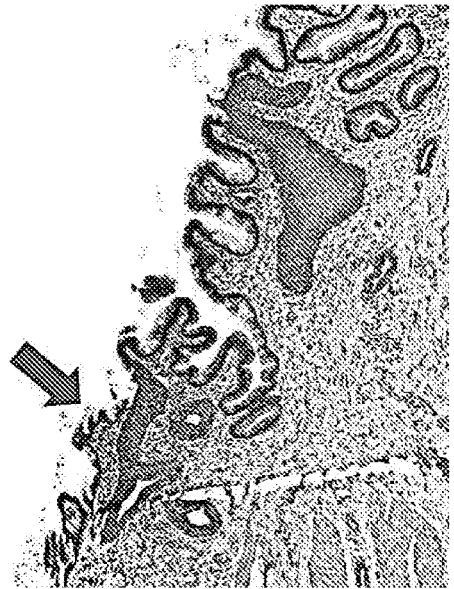
Figure 13A:
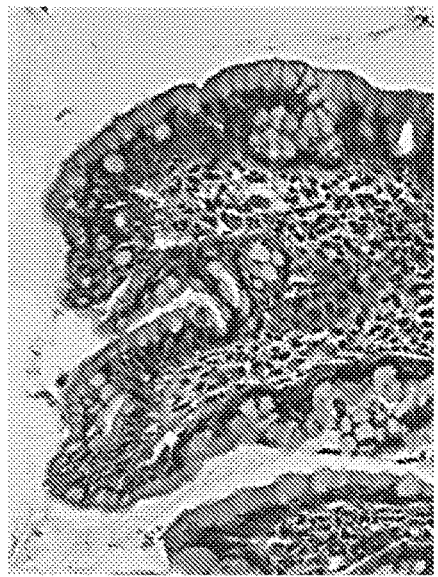
Figure 13C:
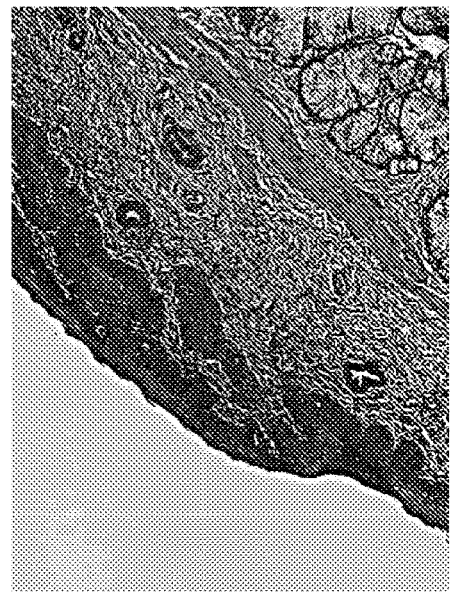

In the animal model before treatment with ECM, both a dog that would be treated with the ECM hydrogel and dog that would not be treated with the ECM hydrogel developed columnar metaplasia (FIGS. 13A and 13B). After treatment with ECM+Omeprazole the treated dog improved and no columnar metaplasia was seen (FIG. 13C). In the control animal, not treated with the ECM hydrogel, there was columnar metaplasia with small patches of squamous epithelium at the same area (FIG. 13D).

Example 3

Treating Stricture with an ECM Hydrogel

Material and Methods

A full circumferential mucosal resection of 5 cm of longitudinal width was performed using a combination of EMR and ESD techniques (Nieponice, 2009, 18657808) in two mongrel dogs. Evaluated treatments were twice daily administration of UBM hydrogel and an untreated control. Endoscopy was performed if animals presented any clinical signs of stricture or had reached 1 month after the procedure. According the endoscopic findings on the animals, a dilation was performed if possible and necessary. Animals were euthanized if they presented severe stricture or reached the 2 month timepoint after the balloon dilation. At the necropsy, animal tissue was measured to determine stricture and samples were harvested for histologic analysis. This animal model allowed measuring the following endpoints:
 1. Endoscopic appearance of resection area
 2. Esophageal measurements
 3. Histologic assessment at final timepoint Surgical Procedure & Postoperative Care Each dog was induced with Acepromazine (0.01 mg/kg, SC) and ketamine (5-11 mg/kg), and surgical plane anesthesia maintained with 1-5% Isofluorane via endotracheal tube. After induction, the animal was moved to the surgery table and positioned inside the sterile surgical theater. Throughout the procedure and observation animals were infused with 2 ml/kg/h of lactated Ringer's solution. Temperature was controlled through warm water recirculating heating pads placed under the animal. Physiologic parameters such as heart, respiration rate, body temperature, and responsiveness were monitored during the procedure. Antibiotic prophylaxis with 25 mg/kg of Cefazolin was administered before starting the procedure.

The animal was placed in supine decubitus with and a Pentax EG3430K endoscope was used to evaluate the esophagus. Distance from the mouth to the GE junction was measured. After identifying reference points in the esophagus, the mucosa and submucosa were separated by with injection of saline using a Olympus Injectorforce 4 mm 23G needle. The full circumference of the mucosa (100%) for a length of 5 cm was removed using the ESD and Loop EMR technique. The ESD technique was done by injecting fluid or ECM into the mucosa/submucosa to separate the mucosa from the submucosa then using an endoscopic TT knife to cut the area. To perform EMR, a Cook Duette Kit with a ligation band was used. The mucosa was then excised with the use of a snare. The area of resection was demarked using Spot Endoscopic Marker.

After the mucosa was removed, during the procedure 50 mL of 12 mg/mL UBM hydrogel were delivered and applied to area of excision using a MILA EDC190 Endoscopic delivery catheter. The animal was maintained under anesthesia for 5 mins to allow gelation of the hydrogel. After the procedure animals were recovered and placed in observation.

Following the surgical procedure and cessation of inhalation anesthesia, animals were continually monitored for 24 hours. Body temperature was determined and recorded every 12 hours. The animals were kept warm and dry to prevent hypothermia and was rotated once per half-hour until they maintained a sternal position.

Dogs were held in single housing with other animals in the room until animals were stable, and then placed in normal living facilities. Buprenorphine (0.005-0.01 mg/kg IM or IV, q12h), was administered following each surgical procedure for 5 days for pain and was continued if signs of pain were present and cephalexin (35 mg/kg q12) for 5 days.

After the procedure and until the end of the study, animals were monitored for signs of esophageal stenosis like decrease in food consumption, loss of body weight, and for signs of distress, as determined by increases in breathing patterns, vocal expression, emetic episodes or difficulty swallowing food and/or decreased activity. If these signs were present, animals were evaluated with a contrast esophagogram and/or endoscopy.

Endoscopic Monitoring & Balloon Dilation

One month after the initial surgical procedure animals underwent a endoscopy procedure if any clinical signs of stricture were present. Additionally, all animals underwent an endoscopic procedure prior to euthanasia. Anesthesia was induced with acepromazine (0.1-0.5 mg/kg) and maintained on isoflurane (1-5%) to perform the endoscopy.

If the animal was diagnosed with a mild or moderate stricture during the endoscopy, a balloon dilation was performed. To perform the dilation procedure an Olympus 20 mm balloon dilator was used. Under endoscopic guidance, the balloon was inflated until moderate or significant amount of resistance could be identified with approximately 10 mL of 0.9% NaCl sterile and was kept inflated for 30-60 seconds. After dilation, 50 mL of ECM was immediately applied to the injured area using a MILA EDC 190 catheter and left to gel for 5 minutes. After the procedure animals were not given access to food or water for at least an hour.

ECM Delivery

ECM was delivered orally to the animals with the use of a 60 ml cathether tip syringe at 15° C. 50 mL were delivered twice daily from day 0 until completion of the study. Animals were not allowed to eat or drink for an hour after each delivery of the hydrogel.

Necropsy

At the moment of necropsy an endoscopy was performed as previously described. Euthanasia was performed by administering Pentobarbital Sodium IV (390 mg/kg BW) under anesthesia. After death was confirmed, the esophagus was harvested maintaining the same dimensions it had in the body. Measurements of the esophagus were taken 0.5 cm apart and recorded.

Figure 14:
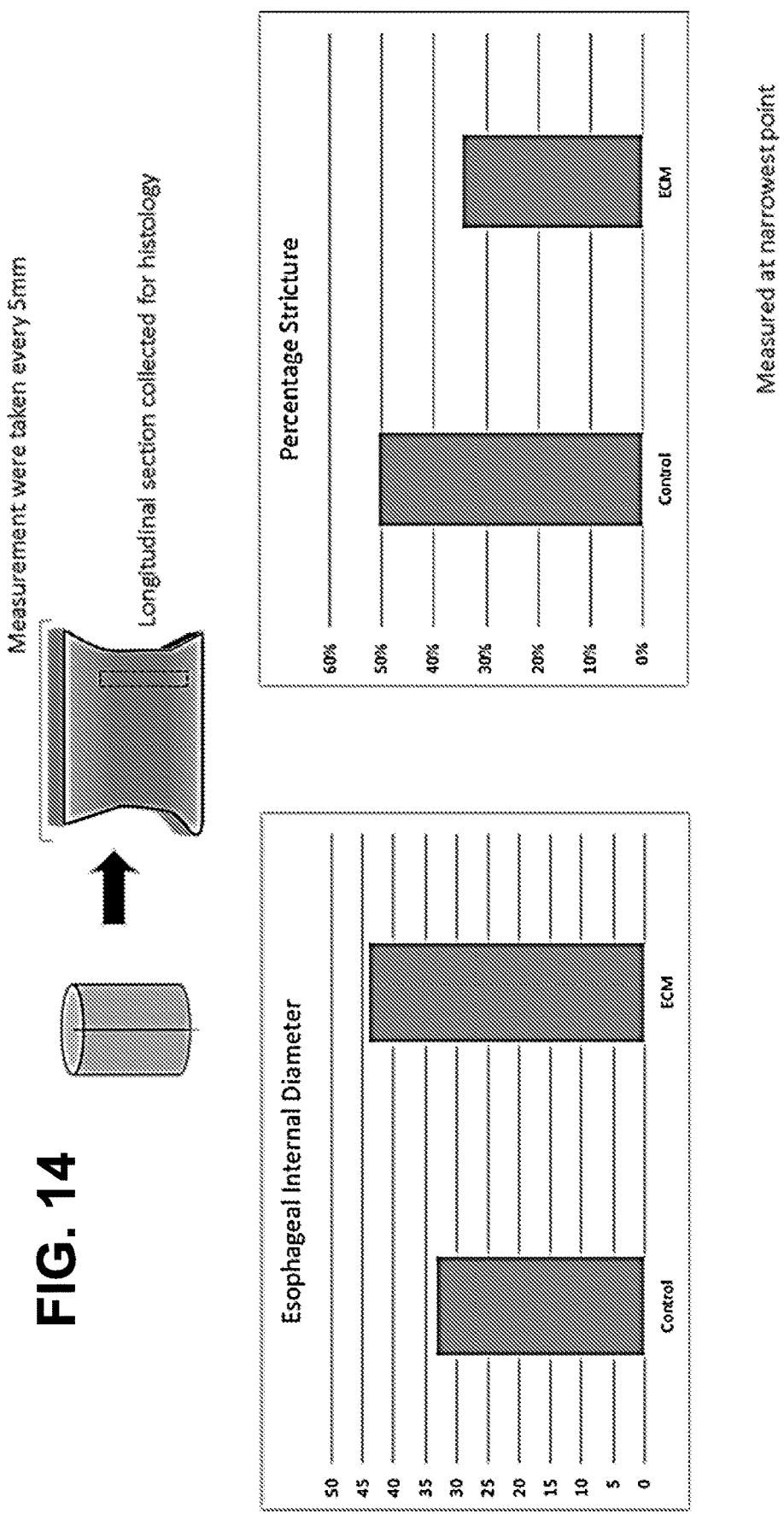
FIG. 14. Use for treating stricture.

The ECM hydrogel treated stricture. As shown in FIG. 14, in a model of full circumferential resection of the mucosa (Different from the Barrett's esophagus model), animals were treated for up to 81 days with ECM hydrogel. A control animal had a severe untreatable stricture and was euthanized after 14 days. An ECM treated animal had esophageal stenosis at 21 days which was dilated. Two months after dilation, the animal was sacrificed and esophageal measurements were taken. The ECM treated animal had a wider internal circumference and a lower decrease in circumference when compared to the control.

Figure 15:
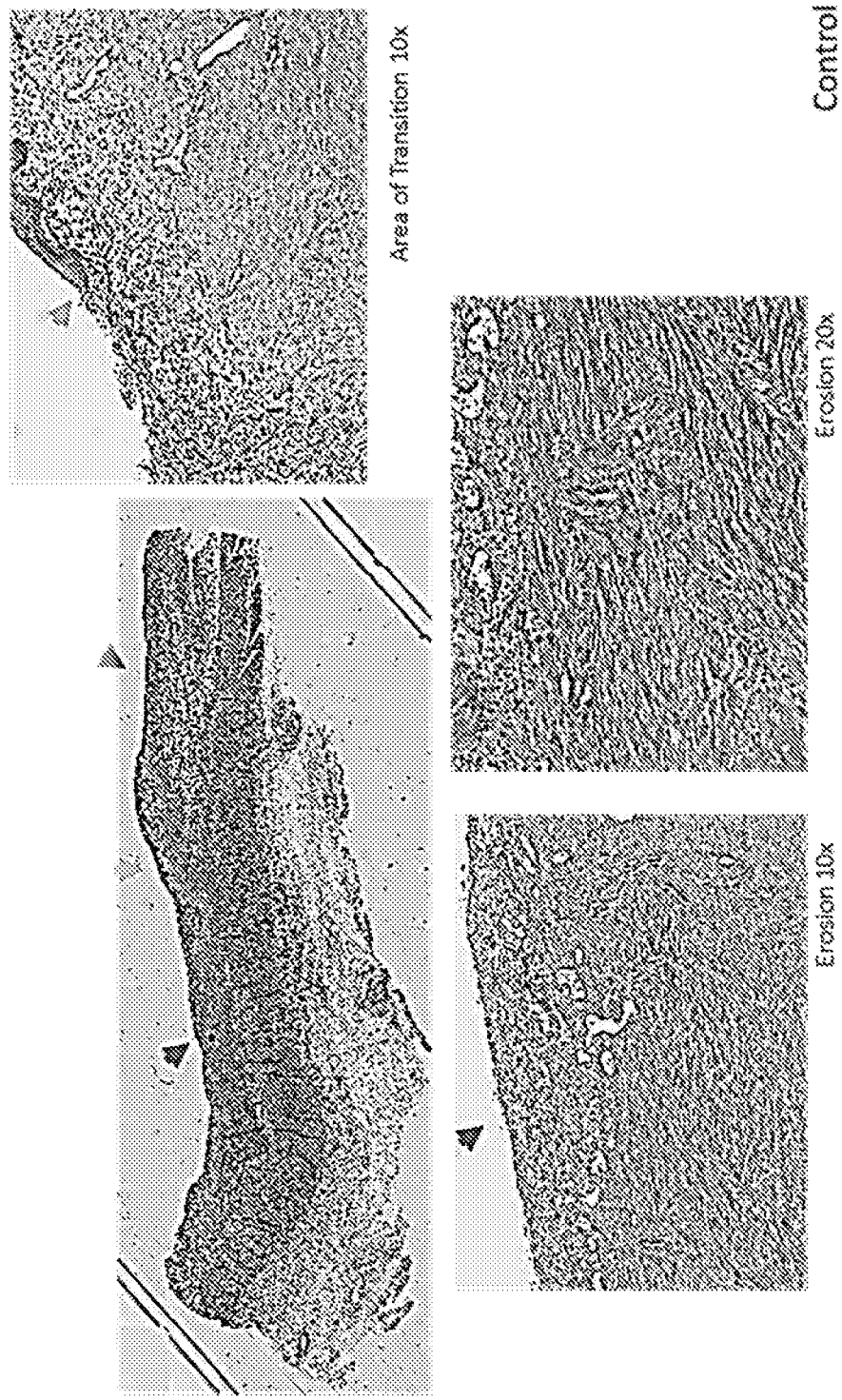
FIG. 15. Histological analysis, control dog.

As shown in FIG. 15, a control animal at 14 days showed disorganized collagen deposition with high cellular infiltration and erosion at the center where the mucosal resection was created. As shown in FIG. 16, treated animals showed re-epithelialization at the center of the defect with lower cellular infiltration and a more organized and dense collagen deposition.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for inhibiting esophageal inflammation or reducing esophageal stricture in a subject, comprising administering to the esophagus of the subject with esophageal inflammation a therapeutically effective amount of an extracellular matrix (ECM) hydrogel, wherein the ECM hydrogel has the following characteristics:
    a) a time to 50% gelation of less than 30 minutes at a temperature of about 37° C.;
    b) a flow viscosity suitable for infusion into the esophagus; and
    c) a stiffness of about 10 to about 300 Pascal (Pa);
    thereby inhibiting esophageal inflammation or reducing esophageal stricture in the subject.

2. The method of claim 1, wherein the time to 50% gelation is about 3 to about 30 minutes at about 37° C.

3. The method of claim 1, wherein the time to 50% gelation is about 3 to about 10 minutes at about 37° C.

4. The method of claim 2, wherein the time to 50% gelation is about 4 to about 10 minutes.

5. The method of claim 1, wherein the flow viscosity is about 1 to about 40 Pa*s at a shear rate of about 0.1/s and is about 0.01 to about 0.2 Pa*s at a shear rate of 1000/s.

6. The method of claim 1, wherein the flow viscosity is about 0.1 to about 25 Pa*s at a shear rate of 1/s, and is about 0.02 to about 0.8 Pa*s at a shear rate of about 100/s.

7. The method of claim 1, wherein the ECM hydrogel has a stiffness of 10-70 Pa.

8. The method of claim 1, wherein the ECM concentration in the ECM hydrogel is 2 mg/ml to about 16 mg/ml.

9. The method of claim 1, wherein the ECM hydrogel is administered orally, endoscopically or via a catheter to the subject.

10. The method of claim 1, wherein the ECM hydrogel is produced by
   (a) solubilizing decellularized extracellular matrix (ECM) by digestion of tissue with an acid protease in an acidic solution to produce digested esophageal ECM; and
   (b) raising the pH of the digested esophageal ECM to a pH between 7.2 and 7.8 to produce a neutralized digest solution.

11. The method of claim 10, wherein (b) raising the pH of the digested ECM comprises adding a base or an isotonic buffer to raise the pH of the digested ECM.

12. The method of claim 10, wherein the acid protease is pepsin, trypsin or a combination thereof.

13. The method of claim 1, wherein the ECM hydrogel is maintained at or below 25° C. prior to administration to the subject.

14. The method of claim 1, wherein the subject has Barrett's esophagus or is at risk of Barrett's esophagus.

15. The method of claim 14, wherein the method inhibits the development of esophageal neoplasia in the subject.

16. The method of claim 1, wherein the ECM hydrogel a) restores the epithelial barrier in the esophagus of the subject; b) increases chemotaxis of both epithelial cells and/or stem cells to the site of injury in the esophagus of the subject; and/or c) reduces esophageal stricture in the subject.

17. A composition comprising an extracellular matrix (ECM) hydrogel, wherein the ECM hydrogel has the following characteristics:
   a) a time to 50% gelation of less than ten minutes at about 37° C.;
   b) a flow viscosity sufficient for injection into the esophagus;
   c) a stiffness of about 10 to about 300 Pascal (Pa); and
   d) the hydrogel is an esophageal hydrogel;
   and wherein the composition is formulated for administration to the esophagus.

18. A kit comprising a) a container, wherein the container comprises the composition of claim 17, or a lyophilized form thereof, and b) instructions for using the composition.

* * * * *

UNITED STATES PATENT AND TRADEMARK OFFICE
CERTIFICATE OF CORRECTION

| | |
|---|---|
| PATENT NO. | : 11,213,545 B2 |
| APPLICATION NO. | : 16/490054 |
| DATED | : January 4, 2022 |
| INVENTOR(S) | : Badylak et al. |

It is certified that error appears in the above-identified patent and that said Letters Patent is hereby corrected as shown below:

In the Claims

Column 24, Line 8, Claim 16, "cells to the site of injury in the esophagus of the subject;" should read --cells to a site of injury in the esophagus of the subject;--.

Signed and Sealed this
Nineteenth Day of April, 2022

Katherine Kelly Vidal
*Director of the United States Patent and Trademark Office*